United States Patent
Yan et al.

(10) Patent No.: US 12,169,204 B2
(45) Date of Patent: Dec. 17, 2024

(54) COUPLED NATIVE MASS SPECTROMETRY FOR ANTIBODY ANALYSIS

(71) Applicant: Regeneron Pharmaceuticals, Inc., Tarrytown, NY (US)

(72) Inventors: Yuetian Yan, Chappaqua, NY (US); Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/527,919

(22) Filed: Dec. 4, 2023

(65) Prior Publication Data

US 2024/0110924 A1 Apr. 4, 2024

Related U.S. Application Data

(63) Continuation of application No. 17/981,839, filed on Nov. 7, 2022, now Pat. No. 11,885,811, which is a continuation of application No. 17/033,820, filed on Sep. 27, 2020, now Pat. No. 11,525,833.

(60) Provisional application No. 62/907,465, filed on Sep. 27, 2019.

(51) Int. Cl.
*G01N 30/72* (2006.01)
*G01N 33/68* (2006.01)
*H01J 49/00* (2006.01)

(52) U.S. Cl.
CPC ......... *G01N 33/6848* (2013.01); *G01N 30/72* (2013.01); *H01J 49/0036* (2013.01)

(58) Field of Classification Search
CPC . G01N 33/6848; G01N 30/72; H01J 49/0036; B01D 15/327

USPC ......................................... 250/281, 282, 288
See application file for complete search history.

(56) References Cited

U.S. PATENT DOCUMENTS

| 7,112,453 | B2 | 9/2006 | Hutchens et al. |
| 2002/0177242 | A1 | 11/2002 | Hutchens et al. |
| 2005/0232929 | A1 | 10/2005 | Kadkhodayan et al. |

FOREIGN PATENT DOCUMENTS

| WO | 1999025877 | 5/1999 |
| WO | WO2017/151892 A2 | 9/2017 |

OTHER PUBLICATIONS

Chen, et al ("Online Hydrophobic Interaction Chromatography—Mass Spectrometry for the Analysis of Intact Monoclonal Antibodies," Anal. Chem. 2018, 90, 7135-7138 (Year: 2018).*

(Continued)

*Primary Examiner* — Michael Maskell
(74) *Attorney, Agent, or Firm* — Kramer Levin Naftalis & Frankel LLP

(57) ABSTRACT

The present invention provides rapid, sensitive high-throughput methods and systems for characterizing peptides or proteins using hydrophobic interaction chromatography-coupled native mass spectrometry to improve manufacturing process of biopharmaceutical products, such as identifying impurities during antibody purification, monitoring post-translational modification variants during production, or characterizing drug-to-antibody ratio of antibody-drug conjugates. The separation profiles of the peptides or proteins are generated and compared to identify or qualify the peptides or proteins.

15 Claims, 32 Drawing Sheets

Specification includes a Sequence Listing.

(56) References Cited

OTHER PUBLICATIONS

Bifan Chen et al: "Online Hydrophobic Interaction Chromatography-Mass Spectrometry for the Analysis of Intact Monoclonal Antibodies", Analytical Chemistry, vol. 90, No. 12, May 30, 2018 (May 30, 2018), pp. 7135-7138.

Canarelli S et al: "On-line microdialysis of proteins with high-salt buffers for direct coupling of electrospray ionization mass spectrometry and liquid chromatography", Journal of Chromatography A, Elsevier, Amsterdam, NL, vol. 948, No. 1-2, Mar. 1, 2002 (Mar. 1, 2002), pp. 139-149.

Rabah Gahoual et al: "Detailed 1-29 Characterization of Monoclonal Antibody Receptor Interaction Using Affinity Liquid Chromatography Hyphenated to Native Mass Spectrometry", Analytical Chemistry, vol. 89, No. 10, May 16, 2017 (May 16, 2017), pp. 5404-5412.

Shen M L et al: "Effect of enzyme inhibitors on protein quaternary structure determined by on-line size exclusion chromatography-microelectrospray ionization mass spectrometry", Journal of the American Society for Mass Spectrometry, Elsevier Science Inc, US, vol. 12, No. 1, Jan. 1, 2001 (Jan. 1, 2001), pp. 97-104.

Leney Aneika C et al: "Native Mass Spectrometry: What is in the Name?", Journal of the American Society for Mass Spectrometry, Elsevier Science Inc, US, vol. 28, No. 1, Dec. 1, 2016 (Dec. 1, 2016), pp. 5-13.

International Search Report, Application No. PCT/US2020/052975, International Filing Date Sep. 27, 2020, date of Mailing Jan. 11, 2021.

Chen, et al ("Online Hydrophobic Interaction Chromatography—Mass Spectrometry for the Analysis of Intact Monoclonal Antibodies" Anal. Chem. Vol. 90, No. 12, May 2018, pp. 7135-7138 (Year: 2018).

Chen, et al ("Online Hydrophobic Interaction Chromatography—Mass Spectrometry for Top-Down Proteonnics" Anal. Chem. 2016, 88, 1885-1891 (Year: 2016).

Tse-Hong Chen et al., Native Reversed-Phase Liquid Chromatography: A Technique for LCMS of Intact Antibody-Drug Conjugates, Anal. Chem., Jan. 21, 2019, vol. 91, pp. 2805-2812.

\* cited by examiner

FIG. 1
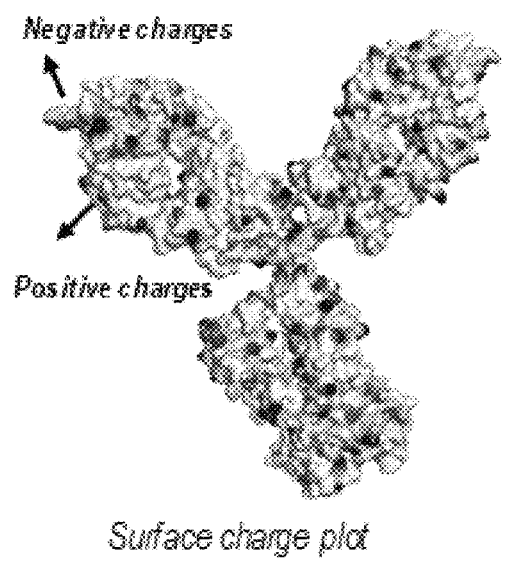
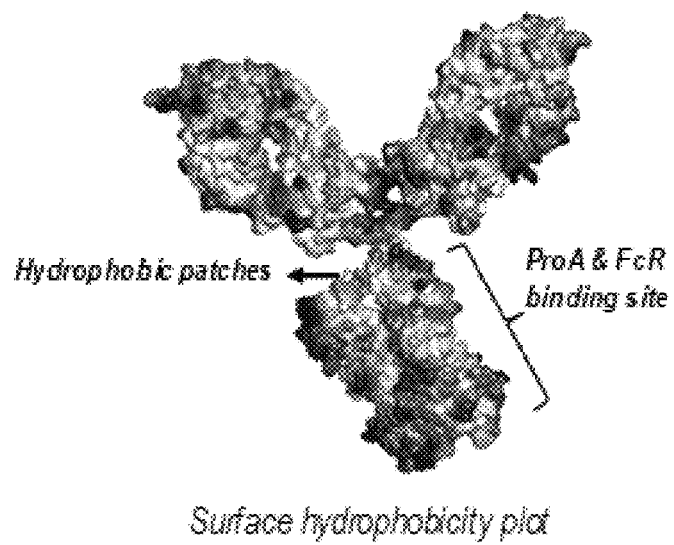

FIG. 3
Flow Path Design A:
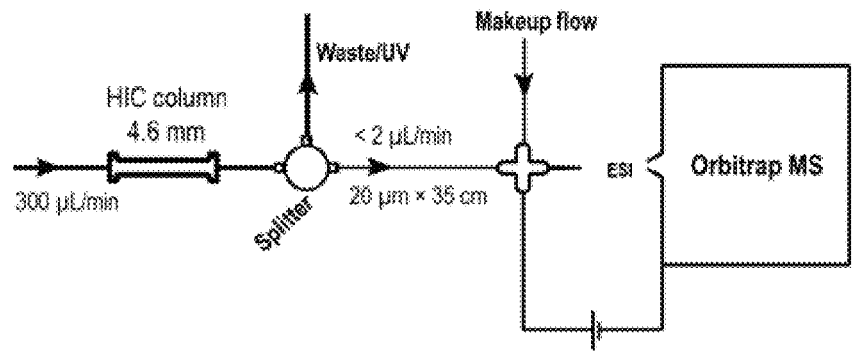
Flow Path Design B:
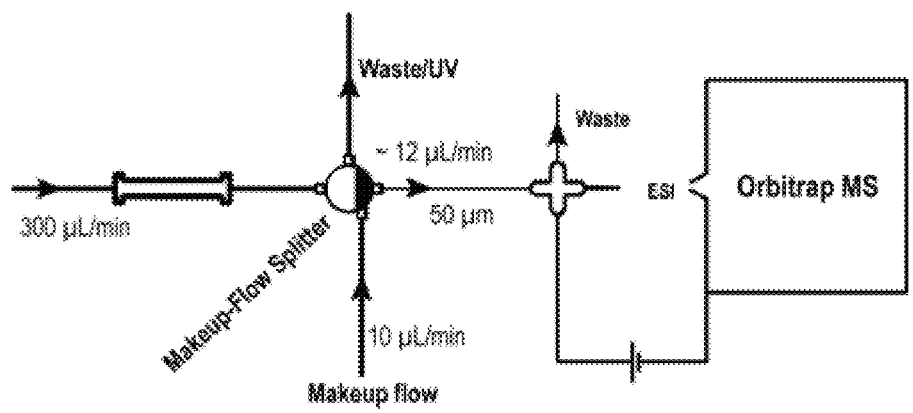
Flow Path Design C:
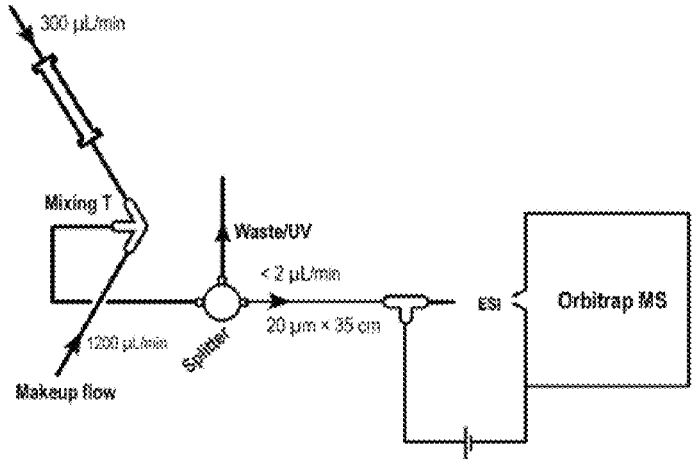

FIG. 4
Design B1:
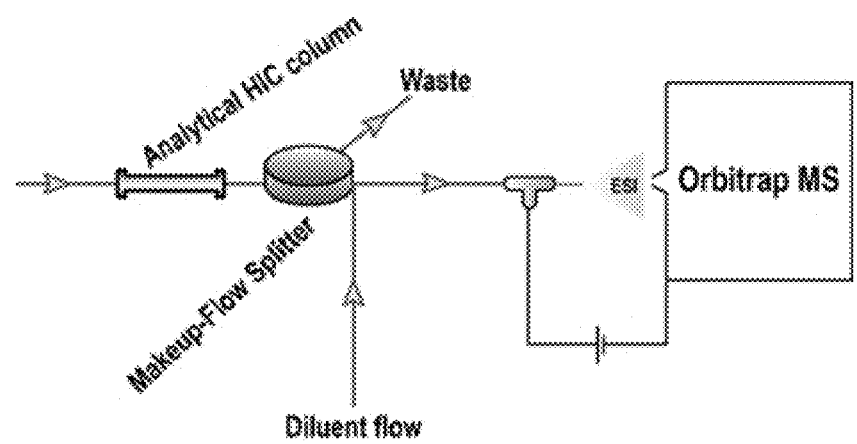
Design B2:
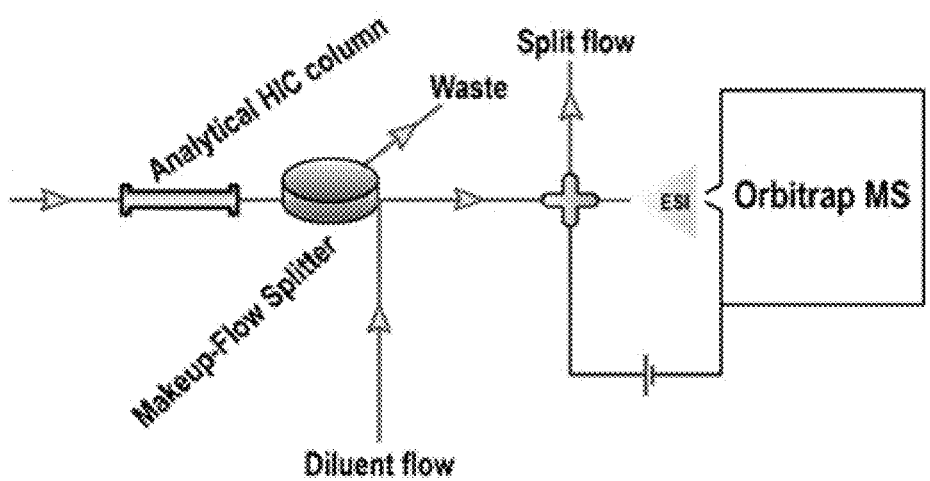

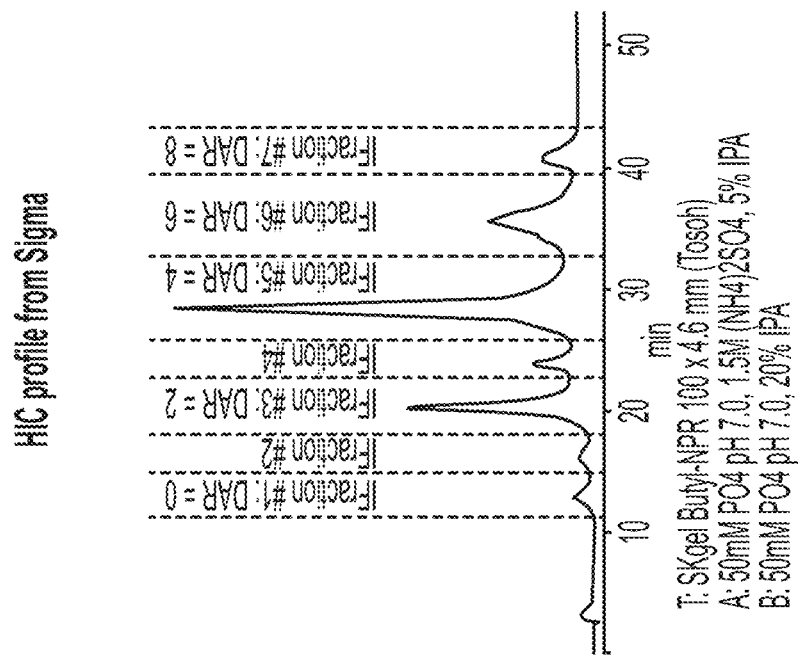
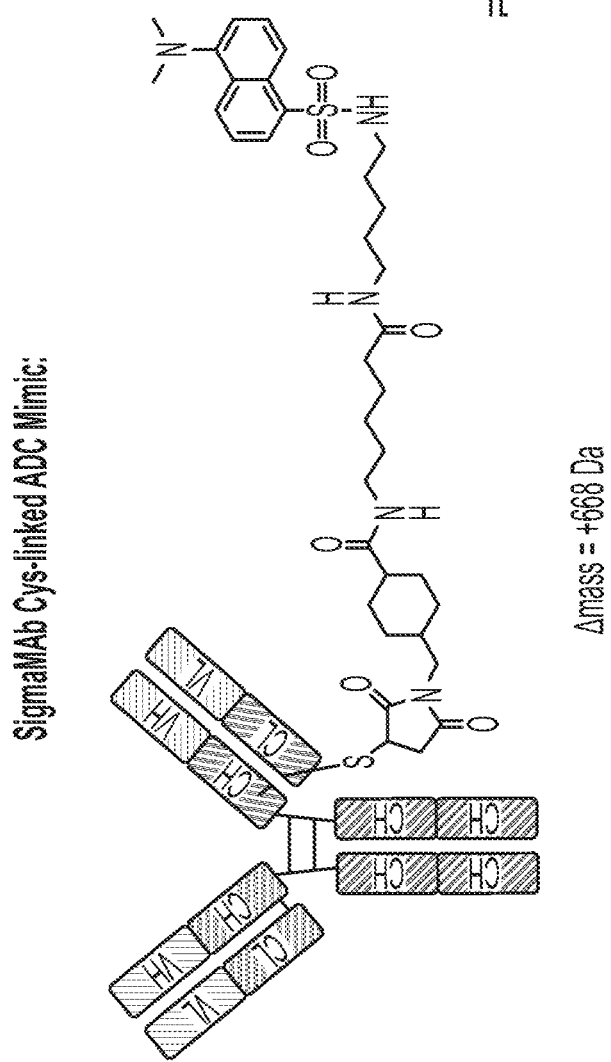
FIG. 11

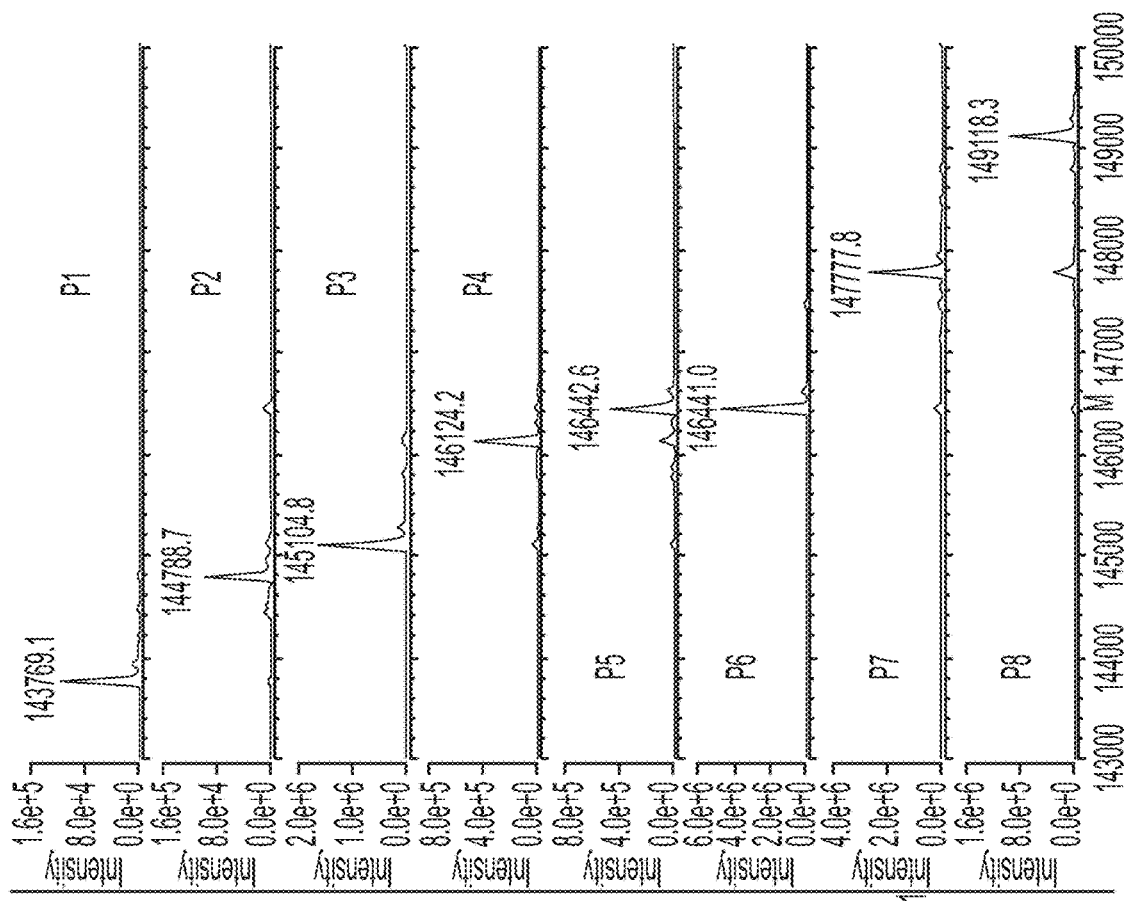
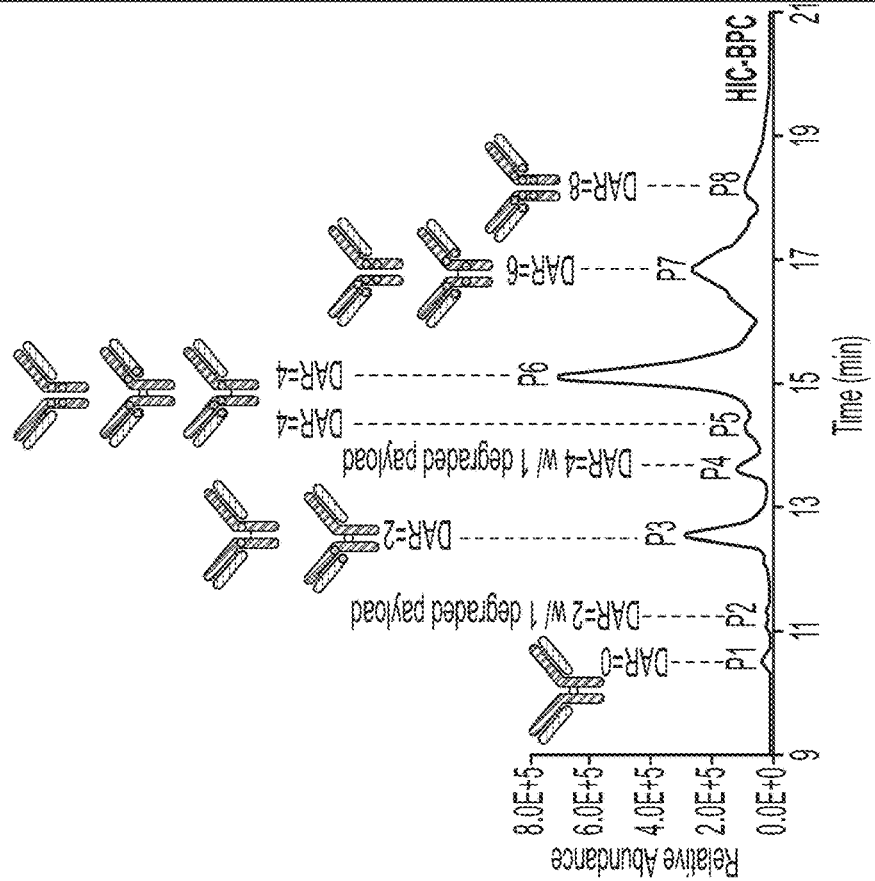
FIG. 11 CONTINUED

FIG. 13
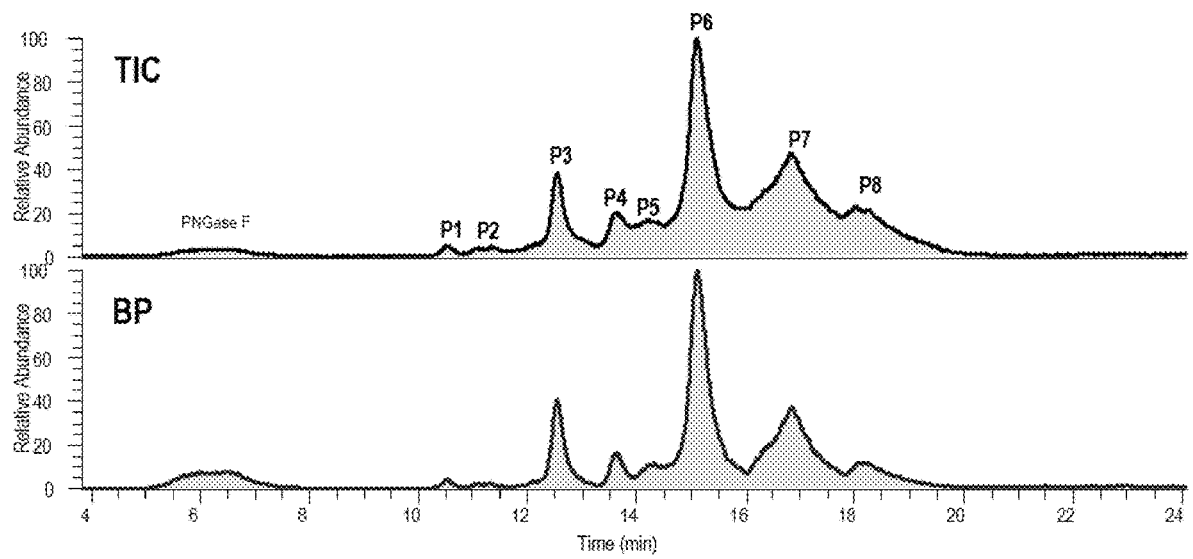
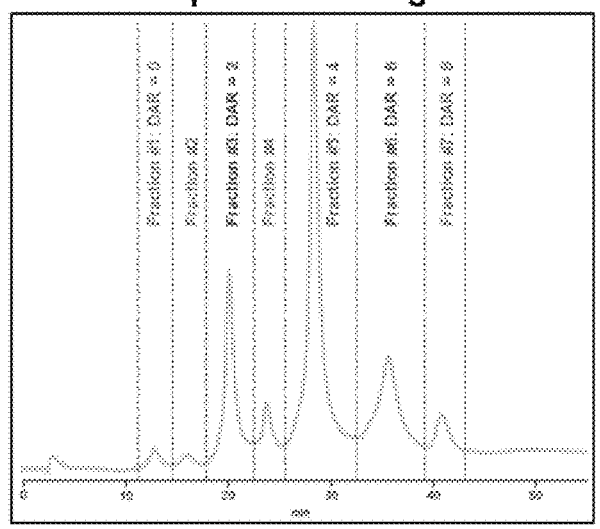

FIG. 16
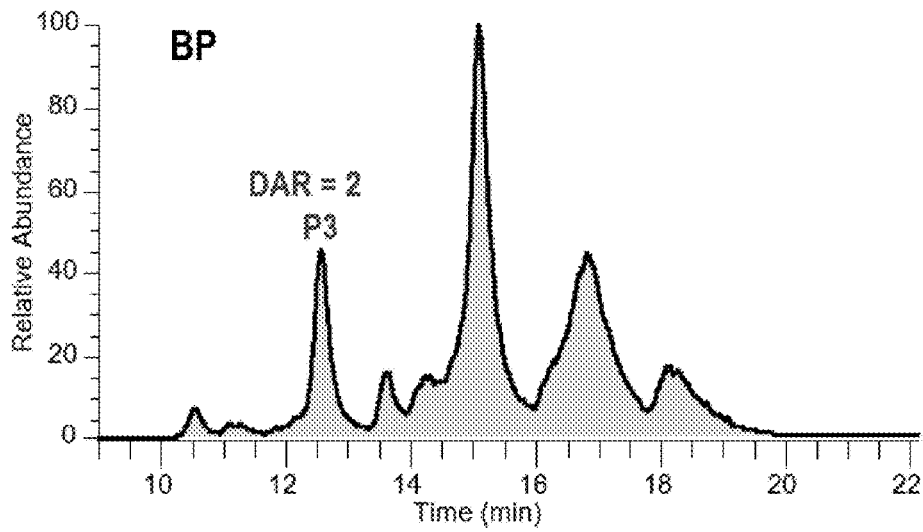
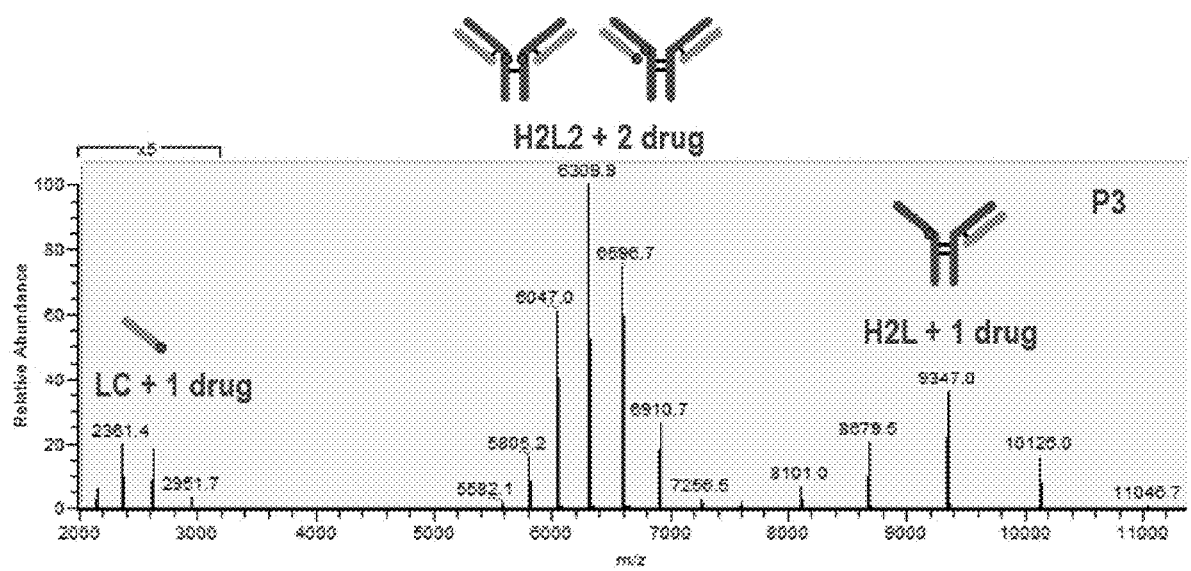

FIG. 17
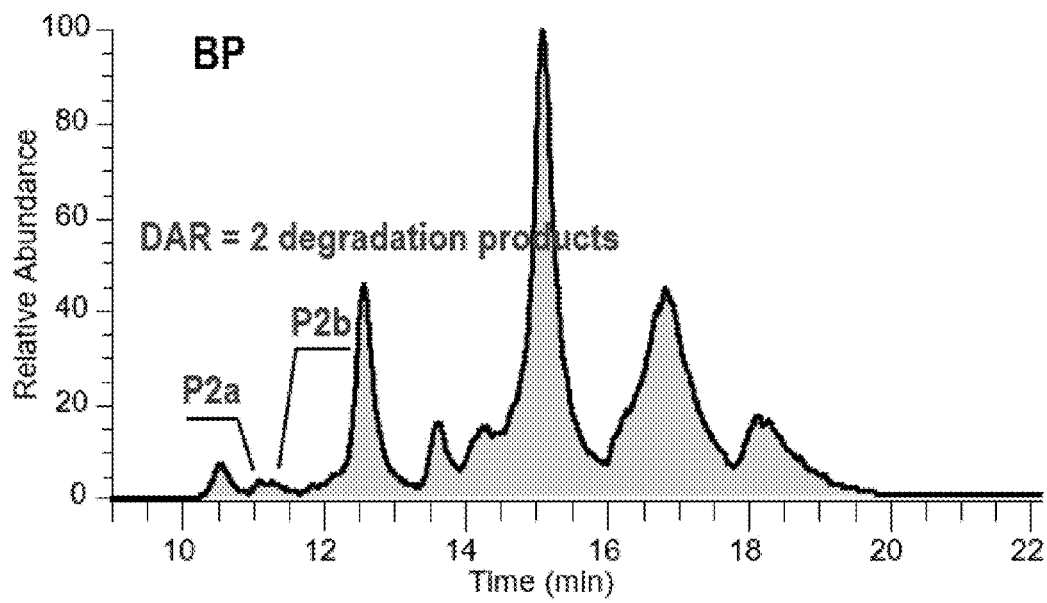
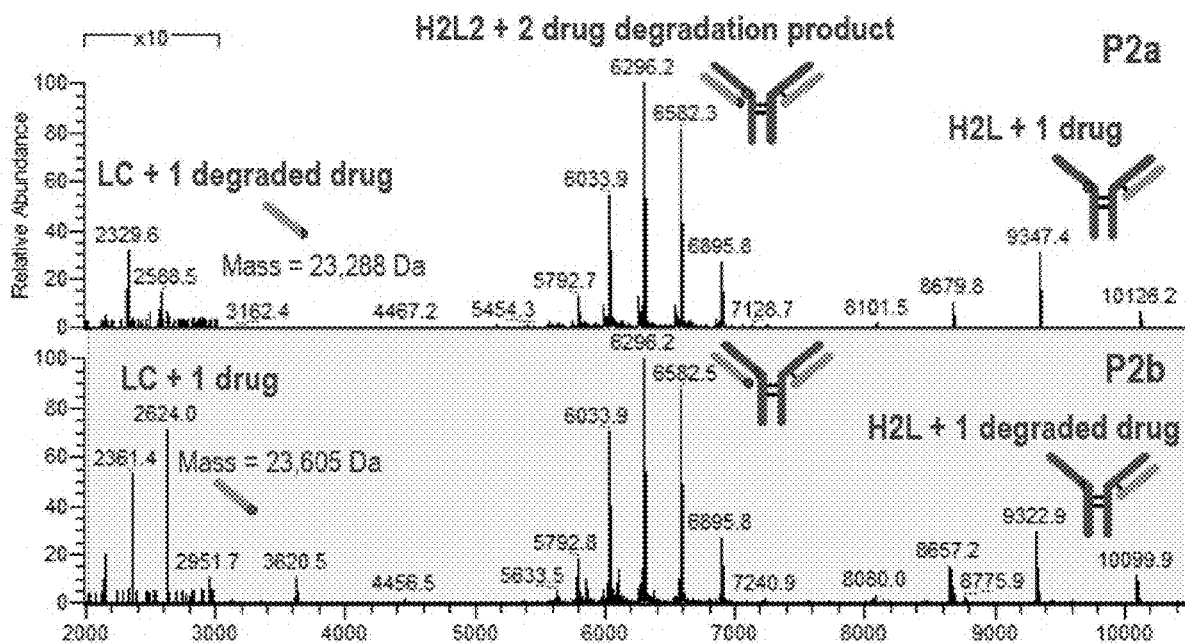

FIG. 18
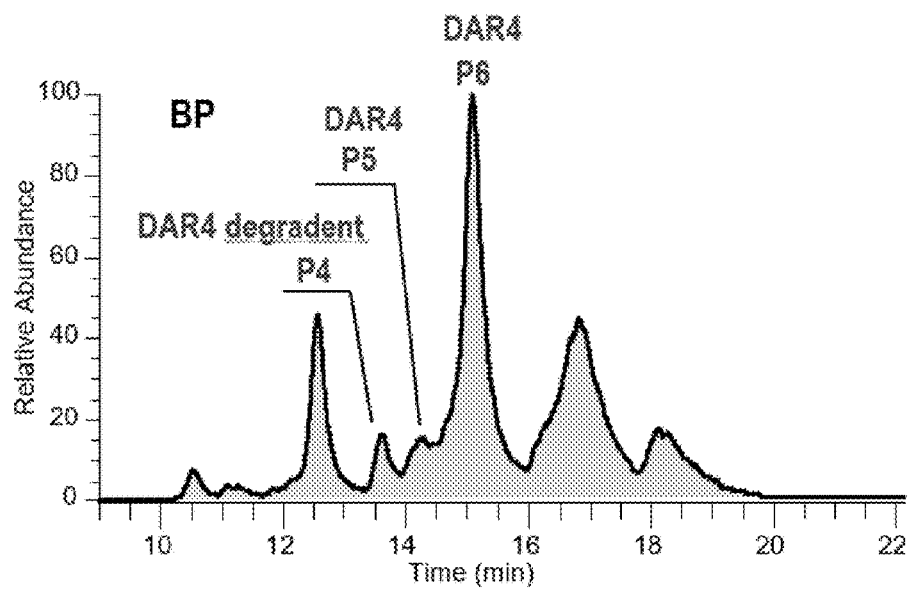
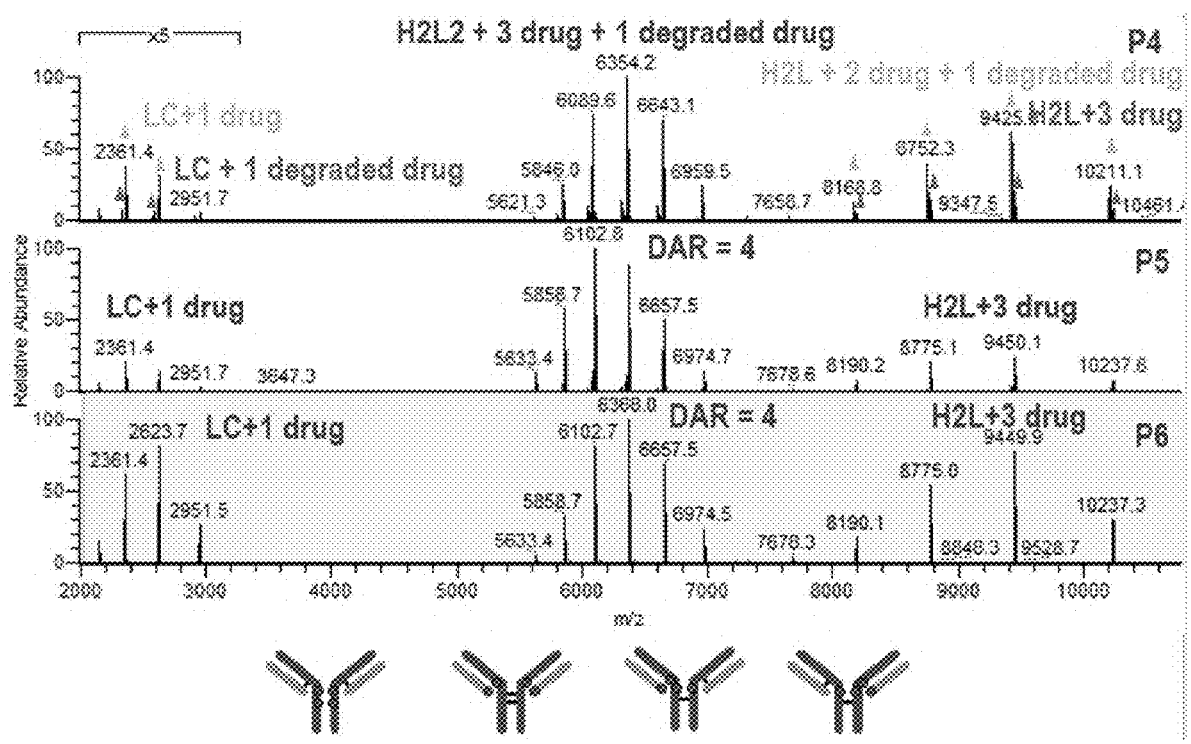

FIG. 19
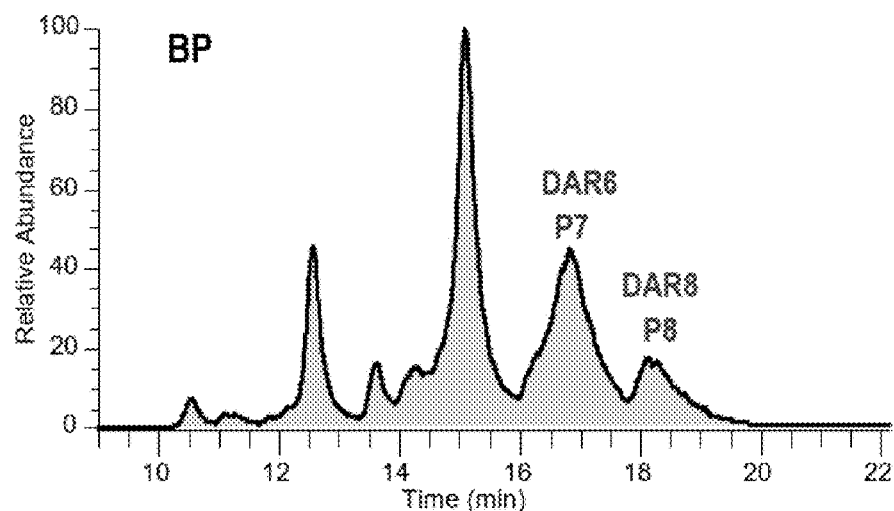
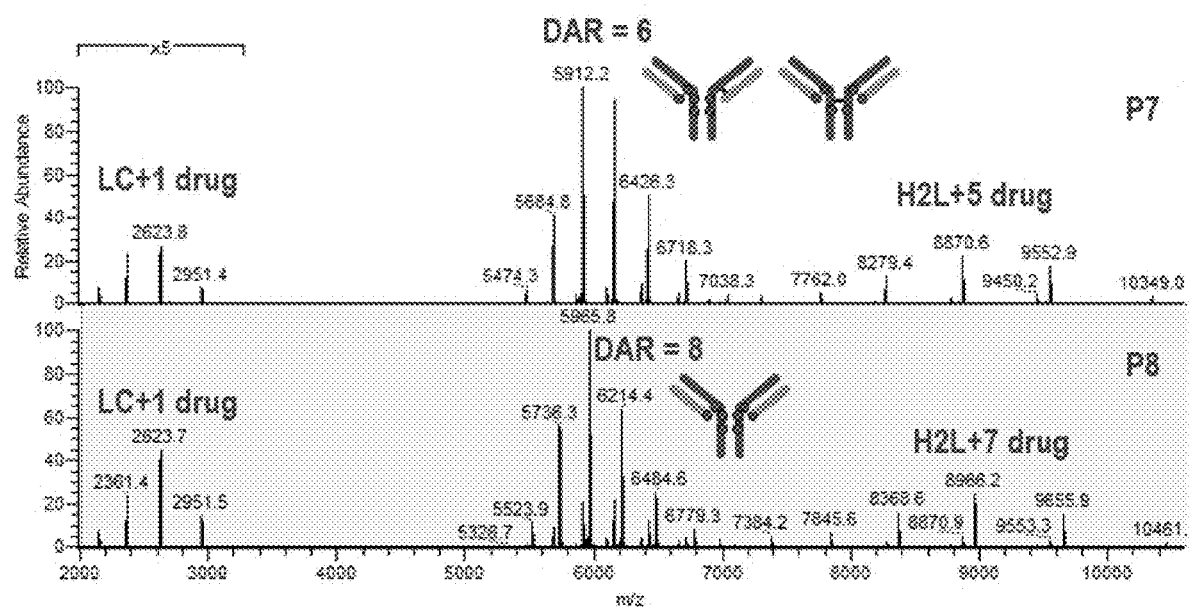

FIG. 20
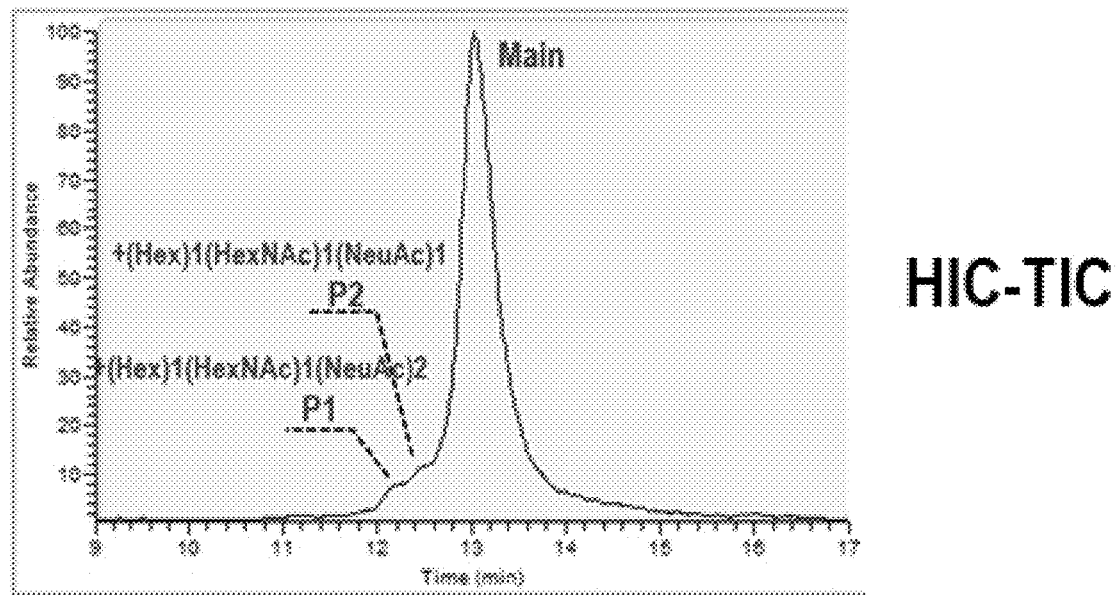
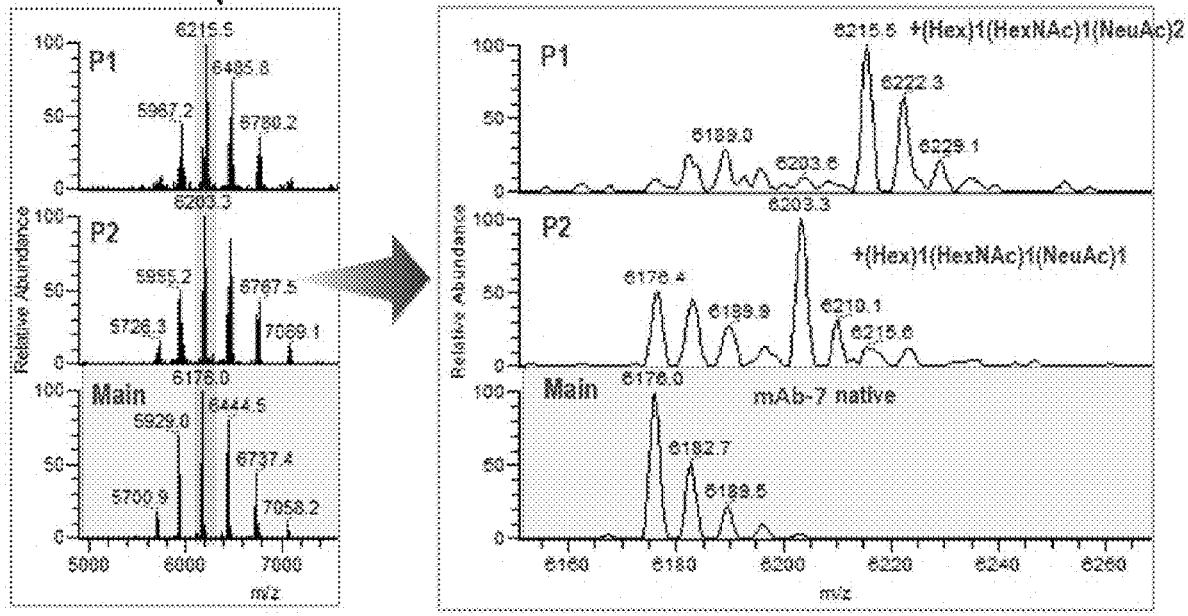

mAb-7 Heavy Chain

```
QLQLQESGPG LVKPSETLSL TCTVSGGSIT SSSYYWGWIR QPPGKGLEWI GSIYYRGSTN 60
YNPSLKSRVT ISVDSSKNQF YLKVSSVTAV DTAVYYCARQ NGAARPSWFD PWGQGTLVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSREEM 360
TKNQVSLTCL VKGFYPSDIA VEWESNGQPE NNYKTTPPVL DSDGSFFLYS KLTVDKSRWQ 420
EGNVFSCSVM HEALHNHYTQ KSLSLSPSK
``` mAb-7 Light Chain

```
EIVLTQSPDT ISLSPGERAT LSCRASQSIS SIYLAWYQQK PGQAPRLLIY GASSRVTGIP 60
DRFSVSGSGT DFTLTISRLE PEDFAVYYCQ HYGISPFTFG PGTKVDIRRT VAAPSVFIFP 120
PSDEQLKSGT ASVVCLLNNF YPREAKVQWK VDNALQSGNS QESVTEQDSK DSTYSLSSTL 180
TLSKADYEKH KVYACEVTHQ GLSSPVTKSF NRGEC 215
```

FIG. 23

FIG. 24
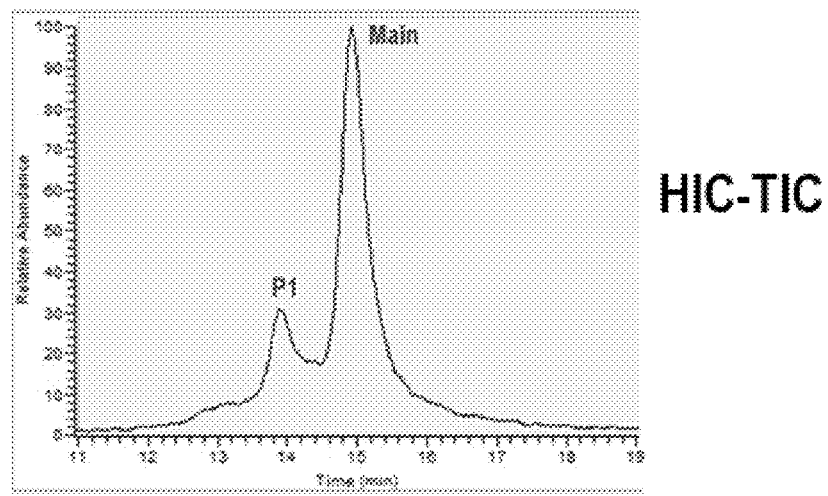
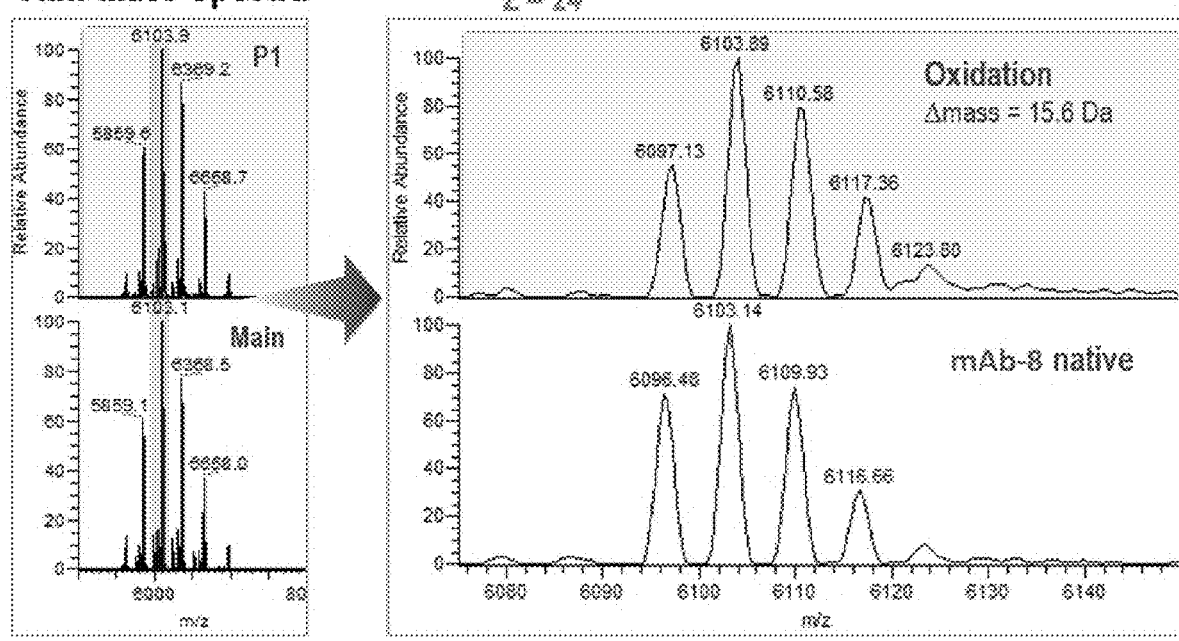

FIG. 25 mAb-8 Ligt Chain

```
DIQMTQSPSS LSASVGDRVT ITCRASQSIS SFLNWYQQKP GKAPKLLIYA ASSLQSGVPS⁶⁰
RFSGSGSGTD FTLTISSLQP EDFATYYCQQ SYSTLTFGQG TRLEIKRTVA APSVFIFPPS¹²⁰
DEQLKSGTAS VVCLLNNFYP REAKVQWKVD NALQSGNSQE SVTEQDSKDS TYSLSSTLTL¹⁸⁰
SKADYEKHKV YACEVTHQGL SSPVTKSFNR GEC²¹³
``` mAb-8 Heavy Chain 

```
EVQLVESGGG LVQPGGSLRL SCAASGFTSS SYAMNWVRQA PGKGLEWVST ISGMGGSTYY⁶⁰
ADSVKGRFTI SRDNSKNTLY LQMNSLRAED TAVYYCAKRG YPHSFDIWGQ GTMVTVSSAS¹²⁰
TKGPSVFPLA PSSKSTSGGT AALGCLVKDY FPEPVTVSWN SGALTSGVHT FPAVLQSSGL¹⁸⁰
YSLSSVVTVP SSSLGTQTYI CNVNHKPSNT KVDKKVEPKS CDKTHTCPPC PAPELLGGPS²⁴⁰
VFLFPPKPKD TLMISRTPEV TCVVVDVSHE DPEVKFNWYV DGVEVHNAKT KPREEQYNST³⁰⁰
YRVVSVLTVL HQDWLNGKEY KCKVSNKALP APIEKTISKA KGQPREPQVY TLPPSRDELT³⁶⁰
KNQVSLTCLV KGFYPSDIAV EWESNGQPEN NYKTTPPVLD SDGSFFLYSK LTVDKSRWQQ⁴²⁰
GNVFSCSVMH EALHNHYTQK SLSLSPGK⁴⁴⁸
```

Reference standard characterization PTM table

| PTMs with Site Location | Lot A | Lot B |
|---|---|---|
| HC C-Terminal Peptide with Lys⁴⁴⁸ | 1.4 | 1.5 |
| Non-Glycosylation at HC Asn²⁹⁸ | 10.0 | 12.8 |
| Deamidation at HC Asn³¹⁶ | <1.0 | <1.0 |
| Deamidation at HC Asn³⁸⁵ | 1.2 | 1.0 |
| Oxidation at HC Met⁸⁴ | 13.6 | 10.5 |
| Oxidation at HC Met¹¹³ | 2.2 | 1.7 |
| Oxidation at HC Met²⁵³ | 4.3 | 3.1 |
| N-terminal pyroglutamate formation at HC Glu¹ | 2.1 | 1.8 |
| Isomerization at HC Asp²⁸¹ | 2.2 | 2.2 |
| Isomerization at HC Asp⁴⁰² | 2.1 | 2.1 |

SEQUENCE LISTING

```
Sequence total quantity: 9
SEQ ID NO: 1           moltype = AA  length = 265
FEATURE                Location/Qualifiers
REGION                 1..265
                       note = Description of Artificial Sequence: Synthetic
                       polypeptide
source                 1..265
                       mol_type = protein
                       organism = synthetic construct
SEQUENCE: 1
```

```
QLQLQESGPG LVKPSETLSL TCTVSGGSIT SSSYYWGWIR QPPGKGLEWI GSIYYRGSTN    60
YNPSLKSRVT ISVDSSKNQF YLKVSSVTAV DTAVYYCARQ NGAARPSWFD PWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVV                                        265

SEQ ID NO: 2            moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 2
TYRVVSVLTV LHQDWLNGKE YKCKV                                         25

SEQ ID NO: 3            moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 3
TKNQVSLTCL VKGFYPSDIA VEWES                                         25

SEQ ID NO: 4            moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 4
EGNVFSCSVM HEALHNHYTQ KSLSLSLGK                                     29

SEQ ID NO: 5            moltype = AA  length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 5
EIVLTQSPDT ISLSPGERAT LSCRASQSIS SIYLAWYQQK PGQAPRLLIY GASSRVTGIP    60
DRFSVSGSGT DFTLTISRLE PEDFAVYYCQ HYGISPFTFG PGTKVDIRRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 6            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 6
GASSRVTGIP                                                          10

SEQ ID NO: 7            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 7
RVTGIPDR                                                             8

SEQ ID NO: 8            moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 8
```

-continued

```
DIQMTQSPSS LSASVGDRVT ITCRASQSIS SFLNWYQQKP GKAPKLLIYA ASSLQSGVPS    60
RFSGSGSGTD FTLTISSLQP EDFATYYCQQ SYSTLTFGQG TRLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 9              moltype = AA  length = 448
FEATURE                   Location/Qualifiers
REGION                    1..448
                          note = Description of Artificial Sequence: Synthetic
                           polypeptide
source                    1..448
                          mol_type = protein
                          organism = synthetic construct
SEQUENCE: 9
EVQLVESGGG LVQPGGSLRL SCAASGFTSS SYAMNWVRQA PGKGLEWVST ISGMGGSTYY    60
ADSVKGRFTI SRDNSKNTLY LQMNSLRAED TAVYYCAKRG YPHSFDIWGQ GTMVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448
```

COUPLED NATIVE MASS SPECTROMETRY FOR ANTIBODY ANALYSIS

CROSS-REFERENCE TO RELATED APPLICATIONS

This application is a continuation of U.S. patent application Ser. No. 17/981,839, filed on Nov. 7, 2022, which is a continuation of U.S. patent application Ser. No. 17/033,820, which is now U.S. Pat. No. 11,525,833, which claims priority to and the benefit of U.S. Provisional Application No. 62/907,465, filed on Sep. 27, 2019, the content of which is incorporated herein by reference in its entirety.

SEQUENCE LISTING

The instant application contains a Sequence Listing which has been submitted electronically in XML format and is hereby incorporated by reference in its entirety. Said XML copy, created on Nov. 7, 2022, is named 070816-02077_SL.xml and is 13,758 bytes in size.

FIELD

The present invention generally pertains to methods and systems for characterizing peptides or proteins using hydrophobic interaction chromatography-coupled native mass spectrometry. The present invention provides rapid sensitive high-throughput methods and systems for characterizing peptides or proteins.

BACKGROUND

Therapeutic peptides or proteins are expressed in cell culture suspension for production. Subsequently, the peptides or proteins are purified to remove process related impurities. The product quality attributes of the purified therapeutic peptides or proteins are extensively characterized to ensure preservation of their associated safety, efficacy, and shelf life profiles relevant to pharmacokinetics.

Alterations of therapeutic peptides or proteins may occur at any point during and after the peptides or proteins are produced and/or purified. The therapeutic peptides or proteins can become heterogeneous due to various post-translational modifications, protein degradation, enzymatic modifications, and chemical modifications. These alterations to the biophysical characteristics of biopharmaceutical products may affect associated safety, efficacy, and shelf life.

It will be appreciated that a need exists for developing high-throughput analytical methods and systems that provide insights to improve the manufacturing process of biopharmaceutical products. It is highly desirable that the analytical method can be conducted in a short period of time to achieve a rapid sensitive high-throughput analytical tool for providing critical improvement for controlling production and purification of high-quality biopharmaceutical products.

SUMMARY

Developing high-throughput analytical methods and systems can be critical for improving manufacturing process of biopharmaceutical products by monitoring production and purification of biopharmaceutical products. This disclosure provides methods and systems to satisfy the aforementioned demands by providing rapid sensitive high-throughput analytical methods and systems based on hydrophobic interaction chromatography-coupled native mass spectrometry to improve manufacturing process of biopharmaceutical products.

The disclosure, at least in part, provides a method for identifying at least one peptide or protein in a sample. In one aspect, the method for identifying at least one peptide or protein in a sample, comprises contacting the sample to a solid surface, wherein the solid surface comprises a hydrophobic group; washing the solid surface using a mobile phase to produce at least one eluent, wherein the eluent comprises the at least one peptide or protein; and characterizing the at least one peptide or protein in the at least one eluent under native conditions using a mass spectrometer.

In some exemplary embodiments, the method for identifying at least one peptide or protein in a sample further comprises generating at least one separation profile.

In some exemplary embodiments, the method for identifying at least one peptide or protein in a sample further comprises identifying or quantifying the at least one peptide or protein based on the at least one separation profile.

In some aspects, the method for identifying at least one peptide or protein in a sample further comprises identifying or quantifying a level of post-translational modification or post-translational modification variation of the at least one peptide or protein based on the at least one separation profile or a comparison with another separation profile.

In some exemplary embodiments, the method for identifying at least one peptide or protein in a sample further comprises identifying or quantifying a level of glycosylation or glycosylation variation of the at least one peptide or protein based on the at least one separation profile or a comparison with another separation profile.

In some exemplary embodiments, the method for identifying at least one peptide or protein in a sample further comprises identifying or quantifying changes of masses or relative hydrophobicity of the at least one peptide or protein based on the at least one separation profile or a comparison with another separation profile.

In some exemplary embodiments, the method for identifying at least one peptide or protein in a sample further comprises separating or identifying an impurity in the sample based on the at least one separation profile or a comparison with another separation profile.

In some aspects, the at least one peptide or protein is a drug, an antibody, a bispecific antibody, a monoclonal antibody, a fusion protein, an antibody-drug conjugate, an antibody fragment, or a protein pharmaceutical product.

In some exemplary embodiments, the method further comprises quantifying a drug-to-antibody ratio of the antibody-drug conjugate based on the at least one separation profile or a comparison with another separation profile.

In some exemplary embodiments, the method for identifying at least one peptide or protein in a sample further comprises identifying or quantifying a drug location, a positional isomer or a degraded payload of the antibody-drug conjugate based on the at least one separation profile or a comparison with another separation profile.

In some exemplary embodiments, the method for identifying at least one peptide or protein in a sample further comprises identifying or quantifying a modification of a complementarity determining region of the antibody, the bispecific antibody, the monoclonal antibody, the antibody-drug conjugate or the antibody fragment based on the at least one separation profile or a comparison with another separation profile.

In some exemplary embodiments, the method for identifying at least one peptide or protein in a sample further comprises a chromatography column that comprises the solid surface and the hydrophobic group.

In some exemplary embodiments, the method for identifying at least one peptide or protein in a sample further comprises a mass spectrometer that is coupled online to the chromatography column.

In some aspects, the hydrophobic group is phenyl, octyl, butyl, hexyl or propyl.

In some exemplary embodiments, the method for identifying at least one peptide or protein in a sample further comprises a splitter that is used to connect the mass spectrometer and the chromatography column.

In some exemplary embodiments, the method for identifying at least one peptide or protein in a sample further comprises a makeup flow, which is introduced to the mobile phase between the mass spectrometer and the chromatography column.

In some exemplary embodiments, the method for identifying at least one peptide or protein in a sample further comprises a splitter that is used to divert a low flow to the mass spectrometer and a high flow to a detector.

In some exemplary embodiments, the method for identifying at least one peptide or protein in a sample further comprises a mass spectrometer that is an electrospray ionization mass spectrometer, nano-electrospray ionization mass spectrometer, a triple quadrupole mass spectrometer, a quadrupole mass spectrometer or a ultra-high mass range hybrid quadrupole mass spectrometer.

In some exemplary embodiments, the method for identifying at least one peptide or protein in a sample further comprises an orbitrap mass analyzer.

The disclosure, at least in part, provides a system for identifying at least one peptide or protein. In one aspect, the system for identifying at least one peptide or protein comprising: a sample comprising the at least one peptide or protein; a chromatography column comprising a hydrophobic group, wherein the chromatography column is capable of being washed by a mobile phase to generate an eluent; a mass spectrometer capable of characterizing or quantifying the at least one peptide or protein, wherein the mass spectrometer is capable of being run under native condition, and being coupled online to the chromatography column.

In some exemplary embodiments, the system for identifying at least one peptide or protein further comprises a splitter that is used to connect the mass spectrometer and the chromatography column.

In some aspects, the system for identifying at least one peptide or protein further comprises a splitter that is used to divert a low flow to the mass spectrometer and to a high flow to a detector.

In some exemplary embodiments, the system for identifying at least one peptide or protein further comprises a mobile phase and the obtained eluent is characterized using the mass spectrometer under native condition.

In some exemplary embodiments, the system for identifying at least one peptide or protein further comprises a makeup flow which is introduced to the mobile phase between the mass spectrometer and the chromatography column.

In some exemplary embodiments, the system for identifying at least one peptide or protein comprises a diode-array detector or a photodiode array detector.

In some exemplary embodiments, the system for identifying at least one peptide or protein further comprises at least one peptide or protein that is a drug, an antibody, a bispecific antibody, a monoclonal antibody, a fusion protein, an antibody-drug conjugate, an antibody fragment, or a protein pharmaceutical product.

In some aspects, the system for identifying at least one peptide or protein further comprises a mass spectrometer that is an electrospray ionization mass spectrometer, nano-electrospray ionization mass spectrometer, a triple quadrupole mass spectrometer, or a ultra-high mass range hybrid quadrupole mass spectrometer.

In some exemplary embodiments, the system for identifying at least one peptide or protein further comprises an orbitrap mass analyzer.

In some exemplary embodiments, the system for identifying at least one peptide or protein comprises a hydrophobic group which is phenyl, octyl, butyl, hexyl or propyl.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows surface charge plot and surface hydrophobicity plot of the molecule structure of antibodies.

FIG. 3 shows flow path designs of systems of the present application, wherein a mass spectrometer is coupled online to a HIC, and wherein a splitter is used to connect the mass spectrometer and the HIC column according to an exemplary embodiment.

FIG. 4 shows variations of flow path design B of the present application, for example, flow path designs B1 and B2 according to an exemplary embodiment.

FIG. 11 shows HIC separation profiles of SigmaMAb Cys-linked ADC mimic provided by Sigma.

FIG. 13 shows the separation profiles of SigmaMAb Cys-linked ADC mimic using the design C of the HIC-native MS of the present application compared to the separation profile provided by Sigma according to an exemplary embodiment.

FIG. 16 shows the separation profiles for characterizing drug locations in SigmaMAb Cys-linked ADC mimic (DAR=2) using in-source dissociation in combination with the HIC-native MS method of the present application according to an exemplary embodiment.

FIG. 17 shows the separation profiles for characterizing positional isomers in SigmaMAb Cys-linked ADC mimic (DAR=2 for degradation products) using in-source dissociation in combination with the HIC-native MS method of the present application according to an exemplary embodiment.

FIG. 18 shows the separation profiles for characterizing drug locations in SigmaMAb Cys-linked ADC mimic (DAR=4) using in-source dissociation in combination with the HIC-native MS method of the present application according to an exemplary embodiment.

FIG. 19 shows the separation profiles for characterizing drug locations in SigmaMAb Cys-linked ADC mimic (DAR=6 or 8) using in-source dissociation in combination with the HIC-native MS method of the present application according to an exemplary embodiment.

FIG. 20 shows the separation profiles of O-glycosylation variants of mAb-7 for characterizing the modifications in CDR including TIC, raw mass spectra and deconvoluted mass spectrum using the HIC-native MS of the present application according to an exemplary embodiment.

FIG. 23 discloses SEQ ID NOS 1-5, respectively, in order of appearance and "GASSRVT-GIP", "(R)VTGIPDR", "(R)VT(+HexNac-Hex-NeuAc)GIPDR" as SEQ ID NOS 6-7 and 7, respectively.

FIG. 24 shows the separation profile of mAb-8 variants using the HIC-native MS of the present application to reveal mass changes corresponding to specific oxidation in CDR in mAb-8 according to an exemplary embodiment.

FIG. 25 shows the analysis of oxidation variants of CDR in mAb-8 using reduced peptide mapping according to an exemplary embodiment. FIG. 25 discloses SEQ ID NOS 8-9, respectively, in order of appearance.

DETAILED DESCRIPTION

Figure 2:
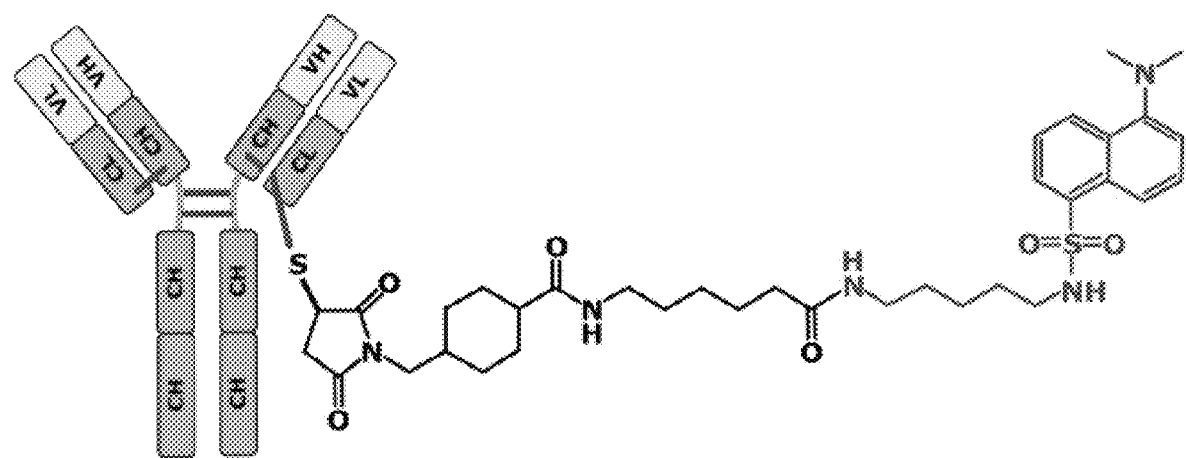
FIG. 2 shows SigmaMAb antibody drug conjugate mimic, for example, SigmaMAb Cys-linked ADC mimic, which contains conjugates by conjugating SigmaMAb (MSQC4), an IgG1 monoclonal antibody, to dansyl fluorophores via an LC-SMCC cross-linker.

The production and manufacturing of biopharmaceutical products are surrounded by various processes and technologies. After the expression and production of the therapeutic peptides or proteins in cell culture suspension, the peptides or proteins can be purified to remove process related impurities. The purified therapeutic peptides or proteins can be extensively characterized to ensure the preservation of their associated safety, efficacy and shelf life profiles relevant to pharmacokinetics and product quality attributes.

Therapeutic peptides or proteins can become heterogeneous due to various post-translational modifications (PTMs), protein degradation, enzymatic modifications, and chemical modifications, which can be introduced at any point during and after the production and purification of peptides or proteins. Identification and characterization of the heterogeneous variants are critical to controlling the quality attributes of the biophysical characteristics of biopharmaceutical products. There are needs in the biopharmaceutical industry for rapid sensitive high-throughput analytical methods to control and monitor the production and purification of therapeutic peptides or proteins, such as the production of monoclonal antibodies or antibody-drug conjugates.

Bispecific antibodies are highly valuable biopharmaceutical products, since they can target two different antigens. The designs of bispecific antibodies can be directed to targeting multiple tissue-specific antibodies combined with use of small molecule drugs, such as combining multiple tissue-specific antibodies and cytotoxic drugs to release drugs in close proximity to tumors. Small drug molecules can be conjugated to the purified bispecific antibodies to produce antibody-drug conjugates (ADC). Expression and purification of bispecific antibodies can be challenging due to the needs of removing impurities, such as removing the parental monospecific antibodies. The monitoring and determination of drug-to-antibody ratios of ADCs is also critical for the quality control of ADCs.

This disclosure provides methods and systems to satisfy the aforementioned demands by providing high-throughput analytical methods and systems based on online hydrophobic interaction chromatography (HIC)-coupled native mass spectrometry (MS) to improve manufacturing process of biopharmaceutical products including identifying impurities during antibody purification, monitoring post-translational modification variants during production, characterizing drug-to-antibody ratio of ADC, characterizing monoclonal antibody mixture for co-formulation, determining relative hydrophobicity, determining intact masses, determining glycosylation profiles, characterizing structural changes or modifications of CDRs (complementarity-determining region) of antibodies, such as oxidation or O-glycans. In particular, the analytic methods and systems of the present application can be sensitive and can be conducted in short period of time to achieve a rapid sensitive high-throughput analytic tool for providing critical improvement in controlling production and purification of biopharmaceutical products.

In observing the surface charge plot and surface hydrophobicity plot of the molecule structure of antibodies as shown in FIG. 1, there are various hydrophobic patches available for separations based on hydrophobic interactions. The hydrophobicity of various monoclonal antibodies can be ranked using relative retention time through HIC analysis. The separation in HIC is based on hydrophobic interactions between the surfaces of an analyte and the stationary phase. Hydrophobic groups, such as phenyl, octyl, butyl, hexyl, or propyl, are incorporated to the stationary phase for chromatography separation. HIC is a widely used offline nondenaturing separation technology for purifying and analyzing monoclonal antibodies. HIC is also widely used for characterizing biologics, such as characterizing fragmentation, misfolding, oxidation of tryptophan or methionine, isomerization of aspartic acid, formation of succinimide or formation of a amidated carboxy terminus. However, there are limitations of HIC to be coupled with native MS for characterizations and separations of peptides or proteins, since high salt concentrations, such as 3M ammonium acetate, are necessary for protein binding in considering protein aggregation. A previous study of online HIC-coupled MS utilizes a special ligand, such as polypentyl, which has increased hydrophobicity to reduce the requirements of high salt concentration in mobile phase. This HIC-coupled MS study utilizes a capillary column format with 1M ammonium acetate in mobile phase A (Chen et al., Online hydrophobic interaction chromatography-mass spectrometry for the analysis of intact monoclonal antibodies, Anal. Chem. 2018, 90, 7135-7138).

This disclosure provides various designs of HIC-coupled native MS with different designs of makeup splitting flows to achieve excellent liquid chromatography performance and high quality mass spectrometry data. The makeup flow of water can be used to dilute the salt concentration of the mobile phase prior to subjecting to electrospray ionization (ESI) or nano-ESI.

Native mass spectrometry is an approach to study intact biomolecular structure in the native or near-native state. The term "native" refers to the biological status of the analyte in solution prior to subjecting to the ionization. Several parameters, such as pH and ionic strength, of the solution containing the biological analytes can be controlled to maintain the native folded state of the biological analytes in solution. Commonly, native mass spectrometry is based on electrospray ionization, wherein the biological analytes are sprayed from a nondenaturing solvent. Other terms, such as noncovalent, native spray, electrospray ionization, nondenaturing, macromolecular, or supramolecular mass spectrometry can also be describing native mass spectrometry. (Leney et al., J. Am. Soc. Mass Spectrom, 2017, 28, pages 5-13, Native Mass Spectrometry: what is in the name)

The present application provides HIC separation coupled with native mass spectrometry based on a rapid online approach, which offers a powerful analytical tool for rapid sensitive high-throughput screening or identification of peptides or proteins. In the methods and systems of the present application, the separation profiles of peptides or protein can be generated based on differential hydrophobic interactions, and subsequently intact biomolecular structures of the peptides or proteins in native or near-native states can be characterized using mass spectrometry.

Among the various detection modes that can be coupled with HIC, mass spectrometry allows precise and accurate identification of individual components in complex samples. Several parameters, such as pH ranges or salt concentrations, of the solution containing the biological analytes should be controlled to maintain the native folded state of the biological analytes for conducting native mass spectrometry. The biological status of the analytes, for example, peptides or proteins, in solution is maintained at the native or native-like folded state after the elution of HIC column and prior to subjecting to the ionization step of mass spectrometry.

The methods and systems of the present application are advantageous for providing high-throughput methods and systems that provide mechanistic insights for improving manufacturing process of therapeutic peptides or proteins. In particular, the present application can provide rapid, sensitive high-throughput methods and systems to characterize antibodies, antibody variants, or antibody-drug conjugates by combining HIC with intact native mass spectrometry.

In one aspect, monoclonal antibodies or antibody variants containing specific post-translational modifications are evaluated using the high-throughput methods and systems of the present application by combining HIC with intact native mass spectrometry. In some preferred exemplary embodiments, the methods and systems of the present application can be used to identify or quantify a level of post-translational modification or post-translational modification variation of the monoclonal antibodies or antibody variants.

In one aspect, monoclonal antibodies or antibody variants containing specific glycosylation are evaluated using the high-throughput methods and systems of the present application by combining HIC with intact native mass spectrometry. In some preferred exemplary embodiments, the methods and systems of the present application can be used to identify or quantify a level of glycosylation or glycosylation variation of the monoclonal antibodies or antibody variants, such as revealing the O-glycosylation modification or oxidation in CDR. In some preferred exemplary embodiments, the methods and systems of the present application can be used to identify or quantify a level of glycosylation or glycosylation variation of the monoclonal antibodies or antibody variants using glycan-based separation or changes of glycoforms.

In one aspect, the present application provides sensitive, high-throughput analytical methods and systems to identify or quantify the drug-to-antibody ratio of an antibody-drug conjugate using the high-throughput methods and systems of the present application by combining HIC with intact native mass spectrometry. In some preferred exemplary embodiments, the antibody-drug conjugate to be analyzed is a lysine-linked or cysteine-linked antibody-drug conjugate. The present application is particularly advantageous by providing high peak capacity coupled with uniform elution of species with different drug-to-antibody ratios in combination with sensitive mass spectrometry detection under native condition.

In one aspect, the present application provides sensitive, high-throughput analytical methods and systems to identify or quantify monoclonal antibodies, antibody variants containing specific glycosylation or monoclonal antibody mixture for co-formulation by combining HIC with intact native mass spectrometry.

Considering the limitations of existing methods, exemplary embodiments disclosed herein satisfy the long felt needs of providing rapid, sensitive high-throughput analytical methods and systems based on HIC-coupled native mass spectrometry to improve manufacturing process of biopharmaceutical products including identifying impurities during antibody purification, monitoring post-translational modification variants during production, characterizing drug-to-antibody ratio of antibody-drug conjugates and characterizing monoclonal antibody mixture for co-formulation.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, the disclosure provides a method for identifying at least one peptide or protein in a sample, comprising: contacting the sample to a solid surface, wherein the solid surface comprises a hydrophobic group; washing the solid surface using a mobile phase to produce at least one eluent, wherein the eluent comprises the at least one peptide or protein; characterizing the at least one peptide or protein in the at least one eluent using a mass spectrometer under native conditions. In some exemplary embodiments, the disclosure provides a system for identifying at least one peptide or protein, comprising: a sample comprising the at least one peptide or protein; a chromatography column comprising a hydrophobic group, wherein the chromatography column is capable of being washed by a mobile phase to generate an eluent; a mass spectrometer capable of characterizing or quantifying the at least one peptide or protein, wherein the mass spectrometer is capable of being run under native conditions, and being coupled online to the chromatography column.

As used herein, the term "native" in the description of "using a mass spectrometer under native conditions" refers to the biological status of the analyte in solution prior to subjecting to the ionization. As used herein, the term "native conditions" or "native mass spectrometry" can include a performing mass spectrometry under conditions that preserve non-covalent interactions in an analyte. For detailed review on native MS, refer to the review: Elisabetta Boeri Erba & Carlo Petosa, The emerging role of native mass spectrometry in characterizing the structure and dynamics of macromolecular complexes, 24 PROTEIN SCIENCE 1176-1192 (2015).

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

In some exemplary embodiments, in the method for identifying at least one peptide or protein in a sample, the at least one peptide or protein is a drug, an antibody, a bispecific antibody, a monoclonal antibody, a fusion protein, an antibody-drug conjugate, an antibody fragment, or a protein pharmaceutical product.

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule. In some exemplary embodiments, the protein can be an antibody, a bispecific antibody, a multispecific antibody, antibody fragment, monoclonal antibody, host-cell protein or combinations thereof.

As used herein, a "protein pharmaceutical product" includes an active ingredient which can be fully or partially biological in nature. In some exemplary embodiments, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In some other exemplary embodiments, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

As used herein, an "antibody fragment" includes a portion of an intact antibody, such as, for example, the Fc region, the antigen-binding, or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

As used herein, the term "antibody-drug conjugate", or "ADC" can refer to an antibody attached to biologically active drug(s) by linker(s) with labile bond(s). An ADC can comprise several molecules of a biologically active drug (or the payload) which can be covalently linked to side chains of amino acid residues of an antibody (Siler Panowski et al., Site-specific antibody drug conjugates for cancer therapy, 6 mAbs 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. Finally, the linker that forms the connection between the payload and the antibody can be capable of being sufficiently stable in circulation to take advantage of the pharmacokinetic properties of the antibody moiety (e.g., long half-life) and to allow the payload to remain attached to the antibody as it distributes into tissues, yet should allow for efficient release of the biologically active drug once the ADC can be taken up into target cells. The linker can be: those that are non-cleavable during cellular processing and those that are cleavable once the ADC has reached the target site. With non-cleavable linkers, the biologically active drug released within the call includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or $V_H$) and a heavy chain constant region. The heavy chain constant region contains three domains, $C_H1$, $C_H2$ and $C_H3$. Each light chain has of a light chain variable region and a light chain constant region. The light chain constant region consists of one domain ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

In some exemplary embodiments, the method for identifying at least one peptide or protein in a sample further comprises identifying or quantifying a level of post-translational modification or post-translational modification variation of the at least one peptide or protein based on the at least one separation profile or a comparison with another separation profile.

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, vitamin C dependent modifications (proline and lysine hydroxylations and carboxy terminal amidation), vitamin K dependent modification wherein vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics Institute Protein Information ResourceSIB Swiss Institute of Bioinformatics, European Bioinformatics Institute Drs—Drosomycin precursor—*Drosophila melanogaster* (Fruit fly)—Drs gene & protein, http://www.uniprot.org/docs/ptm-list (last visited Jan. 15, 2019) for a more detailed controlled vocabulary of PTMs curated by UniProt.

In some exemplary embodiments, the method for identifying at least one peptide or protein in a sample further comprises separating or identifying an impurity in the sample based on the at least one separation profile or a comparison with another separation profile.

As used herein, the term "impurity" can include any undesirable protein present in the protein biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S-S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

In some exemplary embodiments, the solid surface comprising a hydrophobic group is included in a chromatography column.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

In some exemplary embodiments, in the method for identifying at least one peptide or protein in a sample, the mass spectrometer is an electrospray ionization mass spectrometer, nano-electrospray ionization mass spectrometer, a triple quadrupole mass spectrometer, a quadrupole mass spectrometer or a ultra-high mass range hybrid quadrupole mass spectrometer.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "nano-electrospray" refers to electrospray ionization at a very low solvent flow rate, typically hundreds of nanoliters per minute of sample solution or lower, often without the use of an external solvent delivery. The electrospray infusion setup forming a nano-electrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

In some exemplary embodiments, the mass spectrometer comprises an orbitrap mass analyzer.

As used herein, the term "mass analyzer" includes a device that can separate species, that is, atoms, molecules, or clusters, according to their mass. Non-limiting examples of mass analyzers that could be employed for fast protein sequencing are time-of-flight (TOF), magnetic electric sector, quadrupole mass filter (Q), quadrupole ion trap (QIT), orbitrap, Fourier transform ion cyclotron resonance (FTICR), and also the technique of accelerator mass spectrometry (AMS).

EXEMPLARY EMBODIMENTS

Embodiments disclosed herein provide compositions, methods, and systems for identifying at least one peptide or protein in a sample based on HIC-coupled native mass spectrometry.

In some exemplary embodiments, the disclosure provides a method for identifying at least one peptide or protein in a sample, comprising: contacting the sample to a solid surface, wherein the solid surface comprises a hydrophobic group; washing the solid surface using a mobile phase to produce at least one eluent, wherein the eluent comprises the at least one peptide or protein; characterizing the at least one peptide or protein in the at least one eluent using a mass spectrometer under native condition. In some exemplary embodiments, the disclosure provides a system for identifying at least one peptide or protein, comprising: a sample comprising the at least one peptide or protein; a chromatography column comprising a hydrophobic group, wherein the chromatography column is capable of being washed by a mobile phase to generate an eluent; a mass spectrometer capable of characterizing or quantifying the at least one peptide or protein, wherein the mass spectrometer is capable of being run under native condition, and being coupled online to the chromatography column.

In some exemplary embodiments, the method or system for identifying at least one peptide or protein in a sample is based on HIC-coupled native mass spectrometry, wherein a HIC column is coupled online to a native mass spectrometer, wherein a splitter is used to connect the mass spectrometer and the chromatography column. For conducting HIC, a HPLC (high performance liquid chromatography) equipped with a HIC column is used for frontend separations. Mobile phases containing ammonium acetate and/or ammonium sulfate are used for HIC applications. In some exemplary embodiment, the concentration of ammonium acetate or ammonium sulfate is about 0.5-5 M, about 1-4.5 M, about 2-3.5 M, about greater than 3 M or preferable about 3 M.

In some exemplary embodiments, the method or system for identifying at least one peptide or protein in a sample is based on HIC-coupled native mass spectrometry, wherein a HIC column is coupled online to a native mass spectrometer, wherein a splitter is used to connect the mass spectrometer and the chromatography column, wherein a makeup flow is introduced to the mobile phase between the mass spectrometer and the chromatography column. For conducting HIC, a HPLC equipped with HIC column is used for frontend separations, wherein the HIC column comprises a hydrophobic group, such as phenyl, octyl, butyl, hexyl or propyl.

In some exemplary embodiments, the mass spectrometry has an orbitrap mass analyzer and uses electrospray ionization (ESI).

In some exemplary embodiments, a mixing T is added after HIC column before splitter, then a makeup flow is introduced to the mobile phase at mixing T. In some exemplary embodiments, the mobile phase has a flow rate of about 100-500 µL/min, about 200-400 µL/min, about 250-350 µL/min or preferable about 300 µL/min for entering the HIC column. In some exemplary embodiments, the flow rate of the mobile phase after the splitter moving toward the ESI is at about 0.1-3 µL/min, about 0.5-2.5 µL/min, about 0.5-2 µL/min, about 0.5-1.5 µL/min, about 0.5 µL/min, about 1 µL/min, about 1.5 µL/min, about 1.7 µL/min or preferable about less than 2 µL/min. In some exemplary embodiments, the makeup flow has a flow rate of about 100-1500 µL/min, about 250-1500 µL/min, about 300-1500 µL/min, about 800-1500 µL/min, about 1000-1300 µL/min, about 1000 µL/min, about 1100 µL/min, about 1300 µL/min or preferable about 1200 µL/min for entering the mobile phase at mixing T.

In some exemplary embodiments, the method or system for identifying at least one peptide or protein in a sample is based on HIC-coupled native mass spectrometry, wherein a HIC column is coupled online to a native mass spectrometer, wherein a splitter is used to connect the mass spectrometer and the chromatography column, wherein a makeup flow is introduced to the mobile phase between the mass spectrometer and the chromatography column. In some exemplary embodiments, the method for identifying at least one peptide or protein in a sample further comprises identifying or quantifying a level of post-translational modification or post-translational modification variation of the at least one peptide or protein, a level of glycosylation or glycosylation variation of the at least one peptide or protein, changes of masses of the at least one peptide or protein, relative hydrophobicity of the at least one peptide or protein, an impurity in the sample, fragmentations of the at least one peptide or protein, misfolding of the at least one peptide or protein, oxidation of tryptophan or methionine of the at least one peptide or protein, isomerization of aspartic acid of the at least one peptide or protein, formation of succinimide of the at least one peptide or protein, or formation of a amidated carboxy terminus of the at least one peptide or protein based on the at least one separation profile or a comparison with another separation profile.

In some exemplary embodiments, the method or system for identifying at least one peptide or protein in a sample is based on HIC-coupled native mass spectrometry, wherein a HIC column is coupled online to a native mass spectrometer, wherein a splitter is used to connect the mass spectrometer and the chromatography column, wherein a makeup flow is introduced to the mobile phase between the mass spectrometer and the chromatography column, wherein the at least one peptide or protein is an antibody, a bispecific antibody, a monoclonal antibody, an antibody-drug conjugate or an antibody fragment. In some exemplary embodiments, the method for identifying at least one peptide or protein in a sample further comprises quantifying or identifying a drug-to-antibody ratio, a drug location, a positional isomer or a degraded payload of the antibody-drug conjugate based on the at least one separation profile or a comparison with another separation profile.

In some exemplary embodiments, the method for identifying at least one peptide or protein in a sample further comprises identifying or quantifying a modification of a CDR of the antibody, the bispecific antibody, the monoclonal antibody, the antibody-drug conjugate or the antibody fragment based on the at least one separation profile or a comparison with another separation profile, wherein the modification is O-glycosylation or oxidation, such as oxidation of tryptophan or oxidation of methionine.

It is understood that the method or system of the present application is not limited to any of the aforesaid pharmaceutical products, peptides, proteins, antibodies, antibody-drug conjugates, biopharmaceutical products, chromatography column, or mass spectrometer.

The consecutive labeling of method steps as provided herein with numbers and/or letters is not meant to limit the method or any embodiments thereof to the particular indicated order. Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

Material and Workflow
1.1 Antibody Reference Material

NISTmAb was used as antibody reference material. The NISTmAb is a recombinant humanized IgG1κ expressed in murine suspension culture, which is a homodimer of two identical light chains and two identical heavy chains. The NISTmAb has low abundance post-translational modifications including methionine oxidation, deamidation, and glycation. The heavy chains of the NISTmAb have N-terminal pyroglutamination, C-terminal lysine clipping, and glycosylation. The NISTmAb has been extensively characterized and was produced in murine suspension cell culture undergone industry standard upstream and downstream purification to remove process related impurities.

2.1 ADC Reference Material

SigmaMAb antibody drug conjugate mimic (Millipore Sigma Inc.), such as Sigma Cys-linked ADC mimic, was used as ADC reference material. SigmaMAb antibody drug conjugate mimic was utilized as a standard for mass spectrometry and high performance liquid chromatography, which contains conjugates by conjugating SigmaMAb (MSQC4), an IgG1 monoclonal antibody, to dansyl fluorophores via an LC-SMCC cross-linker as shown in FIG. 2.

3.1 Workflows for HIC-Coupled Native Mass Spectrometry for Identification of Peptides or Proteins The present application provides HIC-coupled native mass spectrometry methods and systems, wherein a HIC column was coupled online to a native mass spectrometer with various designs, wherein a splitter was used to connect the mass spectrometer and the HIC as shown in FIG. 3. One of the functions of using a splitter is to slow down the flow rate for entering mass spectrometer. It was necessary to dilute the high salt concentration in the mobile phase of the liquid chromatography prior to subjecting to MS detection. In order to reduce the high salt concentration in mobile phase, at least three workflow designs were generated with minimal dead volume and ammonium acetate based gradient, for example, flow path designs A, B and C, to incorporate makeup and splitting flow designs as shown in FIG. 3. There were variations in design B, e.g., designs B1 and B2 as shown in FIG. 4.

In design A, the makeup flow was introduced to the mobile phase between the splitter and the ESI, for example, after the splitter and before the ESI. In an exemplary embodiment, the waste/UV flow of design A was released from the splitter. The mobile phase of design A had a flow rate of about 300 µL/min for entering a HIC column (about 4.6 mm). The flow rate of the mobile phase after the splitter moving toward the ESI was at about less than 2 µL/min (about 20 µm×35 cm) in design A.

In design B, a makeup-flow splitter was used and the makeup flow was introduced to the mobile phase at the splitter or approximately immediately after the splitter. The waste/UV (or waste) flow of design B was released from the splitter and/or before ESI. The variations of design B, e.g., B1 and B2, are shown in FIG. 4. The mobile phase had a flow rate of about 300 µL/min for entering a HIC column (about 4.6 mm) in design B. The flow rate of the mobile phase after the splitter moving toward the ESI was at about 12 µL/min (50 µm) in design B. The makeup flow of design B had a flow rate of about 10 µL/min for entering the splitter.

In design C, a mixing T was added after HIC column before splitter, then the makeup flow was introduced to the mobile phase at mixing T. The waste/UV flow of design C was released from the splitter. The mobile phase had a flow rate of about 300 µL/min for entering a HIC column (about 4.6 mm) in design C. The flow rate of the mobile phase after the splitter moving toward the ESI was at about less than 2 µL/min (about 20 µm×35 cm) in design C. The makeup flow of design C had a flow rate of about 1200 µL/min for entering the mobile phase at mixing T.

An analytical scale HIC column with diameter about 4.6 mm was used to couple with mass spectrometer. Mobile phase A containing high concentration of ammonium acetate, such as greater than 3M, was used to retain monoclonal antibodies or ADC on the HIC column. NanoESI-MS was applied to improve the detection sensitivity and to tolerate high salt concentration. The mass spectrometry analysis in the method or system was conducted under native conditions.

For conducting native mass spectrometry, a Thermo Scientific™ Q-Exactive™ UHMR (ultrahigh mass range) mass spectrometer was used. The mass spectrometer has an orbitrap mass analyzer and uses electrospray ionization (ESI). Mass spectrometry compatible mobile phases containing ammonium acetate were used for HIC. A post-column splitter was used to divert low flow to the mass spectrometer, which was equipped with a Nanospray Flex™ Ion Source which allowed achieving the sensitivity and dissolvation of nanospray ionization source. Raw mass spectrometry spectral data were deconvoluted using INTACT MASS™ software from Protein Metrics.

Example 1. Testing Flow Path Designs

Figure 5:
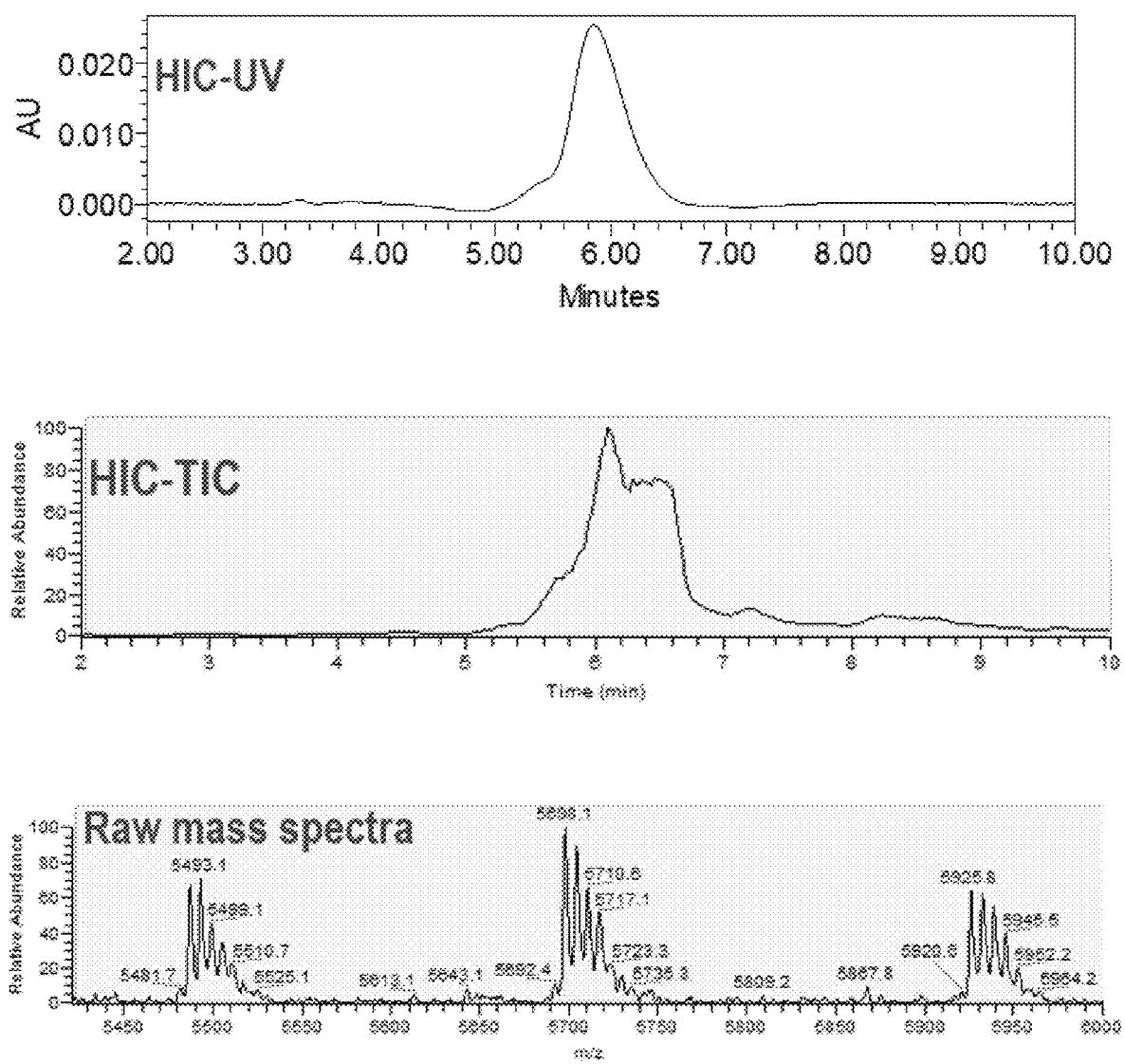
FIG. 5 shows testing results of flow path design A of the present application as the separation profiles regarding HIC-UV (ultraviolet), HIC-TIC (total ion chromatogram) and raw mass spectra according to an exemplary embodiment.

The flow path designs with different makeup and splitting flow designs were tested using an analytical scale HIC column with about 4.6 mm diameter. The testing results of design A were shown in FIG. 5 as the separation profiles regarding HIC-UV (ultraviolet), HIC-TIC (total ion chromatogram) and raw mass spectra. The design A had inconsistent makeup flow delivery through syringe pump. Since the pressure from makeup mixing caused non-flow from splitter to backflow, it resulted poor TIC. In addition, the inefficient mixing caused poor desolvation which led to poor quality of MS data.

Figure 6:
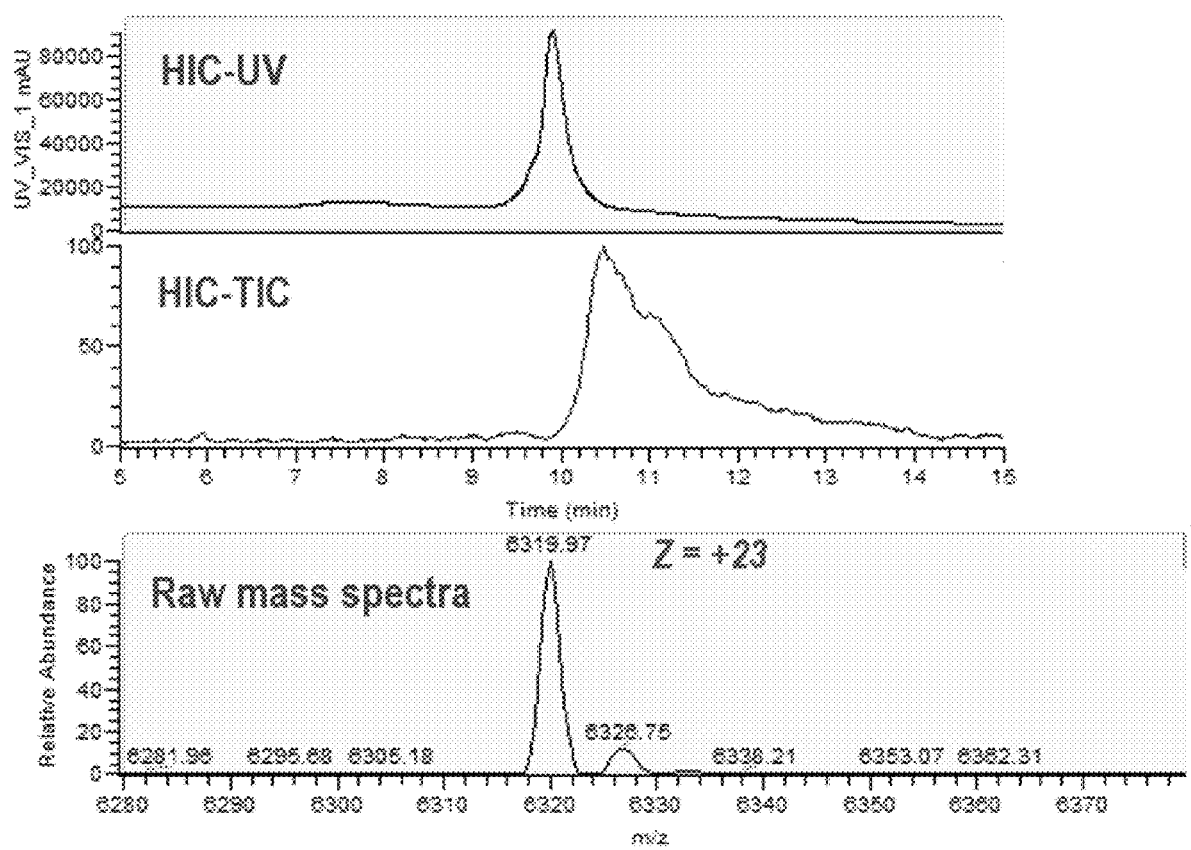
FIG. 6 shows testing results of flow path design B1 of the present application as the separation profiles regarding HIC-UV, HIC-TIC and raw mass spectra according to an exemplary embodiment.
Figure 7:
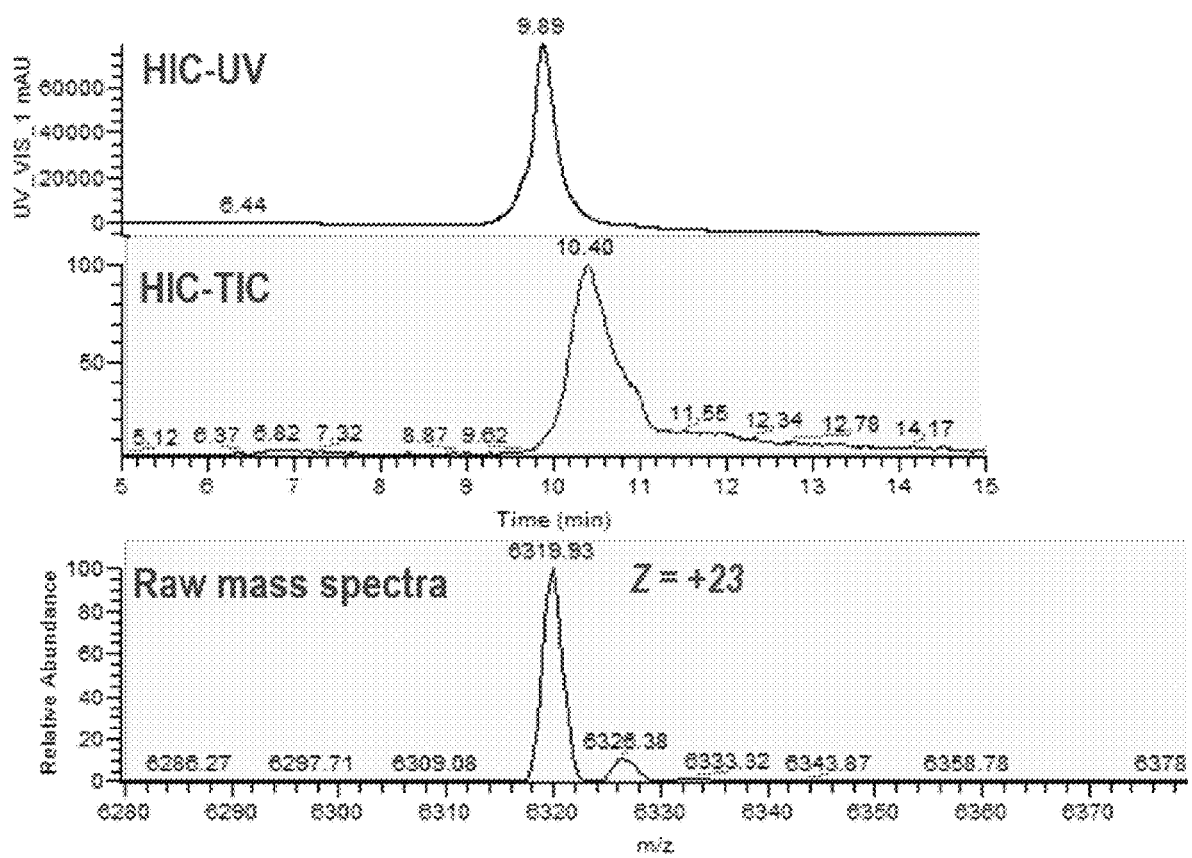
FIG. 7 shows testing results of flow path design B2 of the present application as the separation profiles regarding HIC-UV, HIC-TIC and raw mass spectra according to an exemplary embodiment.
Figure 8:
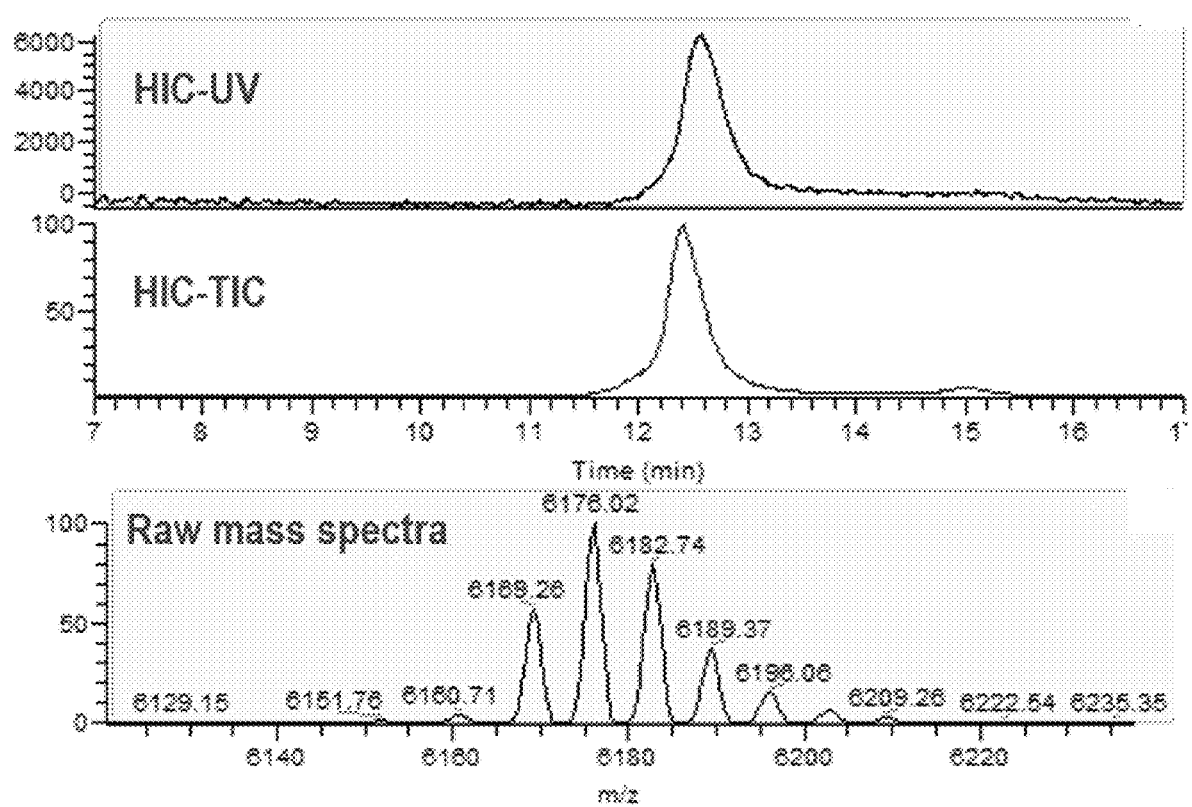
FIG. 8 shows testing results of flow path design C of the present application as the separation profiles regarding HIC-UV, HIC-TIC and raw mass spectra according to an exemplary embodiment.

The testing results of designs B1 and B2 were shown in FIG. 6 and FIG. 7 respectively as the separation profiles regarding HIC-UV, HIC-TIC and raw mass spectra. The testing results of design C were shown in FIG. 8 as the separation profiles regarding HIC-UV, HIC-TIC and raw mass spectra. The design C had good UV and TIC resemblance with good quality and sensitivity of MS data. The UV signal was lower due to dilution and splitting.

Example 2. Screening of NISTmAb

The methods and systems of HIC-coupled native mass spectrometry (HIC-native MS) of the present application were used to identify and screen NISTmAb. The analysis using mass spectrometer was performed under native conditions. A mass spectrometer was coupled online to a HIC column, wherein a splitter was used to connect the mass spectrometer and the HIC column as shown in design C in FIG. 3 and as described in the workflow section. Mass spectrometry compatible mobile phases containing ammonium acetate were used for HIC separation to generate eluents containing NISTmAb which were subsequently subjected to native mass spectrometry analysis. NISTmAb reference material was separated and screened with the rapid high-throughput analytic method of the present application.

Figure 9:
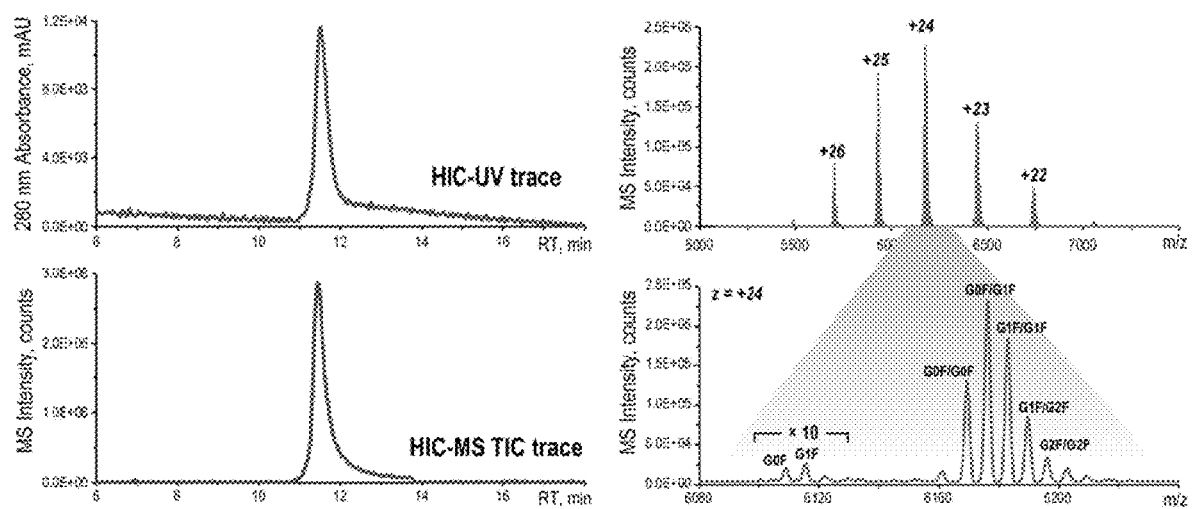
FIG. 9 shows fast screening of NISTmAb reference material with baseline resolution of glycoforms and accurate mass measurement using the online HIC-native MS of the present application according to an exemplary embodiment.

Fast screening of NISTmAb reference material with baseline resolution of glycoforms and accurate mass measurement was accomplished using the online HIC-native MS of the present application as shown in FIG. 9 using design C. NISTmAb is a recombinant humanized IgG1κ expressed in murine suspension culture, which has low abundance post-translational modifications including methionine oxidation, deamidation, and glycation. In addition, the heavy chains of the NISTmAb have N-terminal pyroglutamination, C-terminal lysine clipping, and glycosylation. The variations of post-translational modifications and glycosylation of NISTmAb were well characterized with baseline resolution. Despite the high concentration of salt was required for using the HIC column, native-like charge states of the NISTmAb were maintained across the separation profile which indicated negligible sample denaturation using the method and system of the present application. The results indicate good chromatographic performance and MS data quality.

Example 3. Analysis of Monoclonal Antibody Mixture

Figure 10:
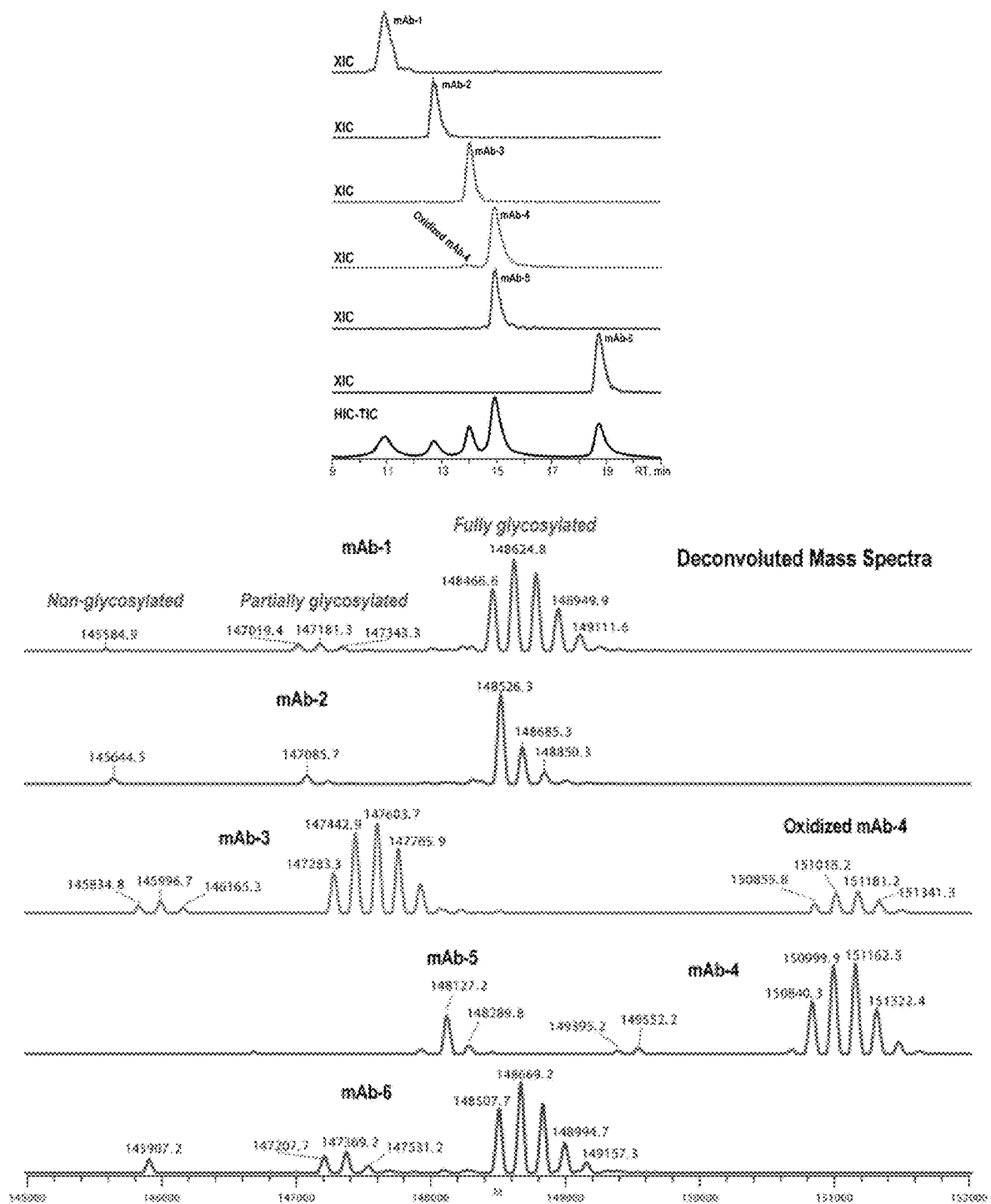
FIG. 10 shows the separation and detection of the glycosylation variations in the antibody mixture containing six different monoclonal antibodies using the HIC-native MS of the present application according to an exemplary embodiment.

The antibody mixture containing six different monoclonal antibodies were subjected to the HIC-native MS of the present application. The analysis using mass spectrometer was performed under native conditions. A mass spectrometer was coupled online to a HIC column, wherein a splitter was used to connect the mass spectrometer and the HIC column as shown in design C in FIG. 3 and as described in the workflow section. Mass spectrometry compatible mobile phases containing ammonium acetate were used for HIC separation to generate eluents containing the monoclonal antibodies. As shown in FIG. 10, the glycosylation variations of the monoclonal antibodies, such as non-glycosylated, partially glycosylated, fully glycosylated, or oxidation, can be separated and detected with good resolution.

The HIC-native MS of the present application provided shorter time for liquid chromatography, which can be considered as high throughput. The testing results had good peak shape with robust chromatography which was suitable for method transfer. In addition, the results provided good quality of MS data for unambiguous online detection.

Example 4. Analysis of Cys-Linked ADC

Figure 12:
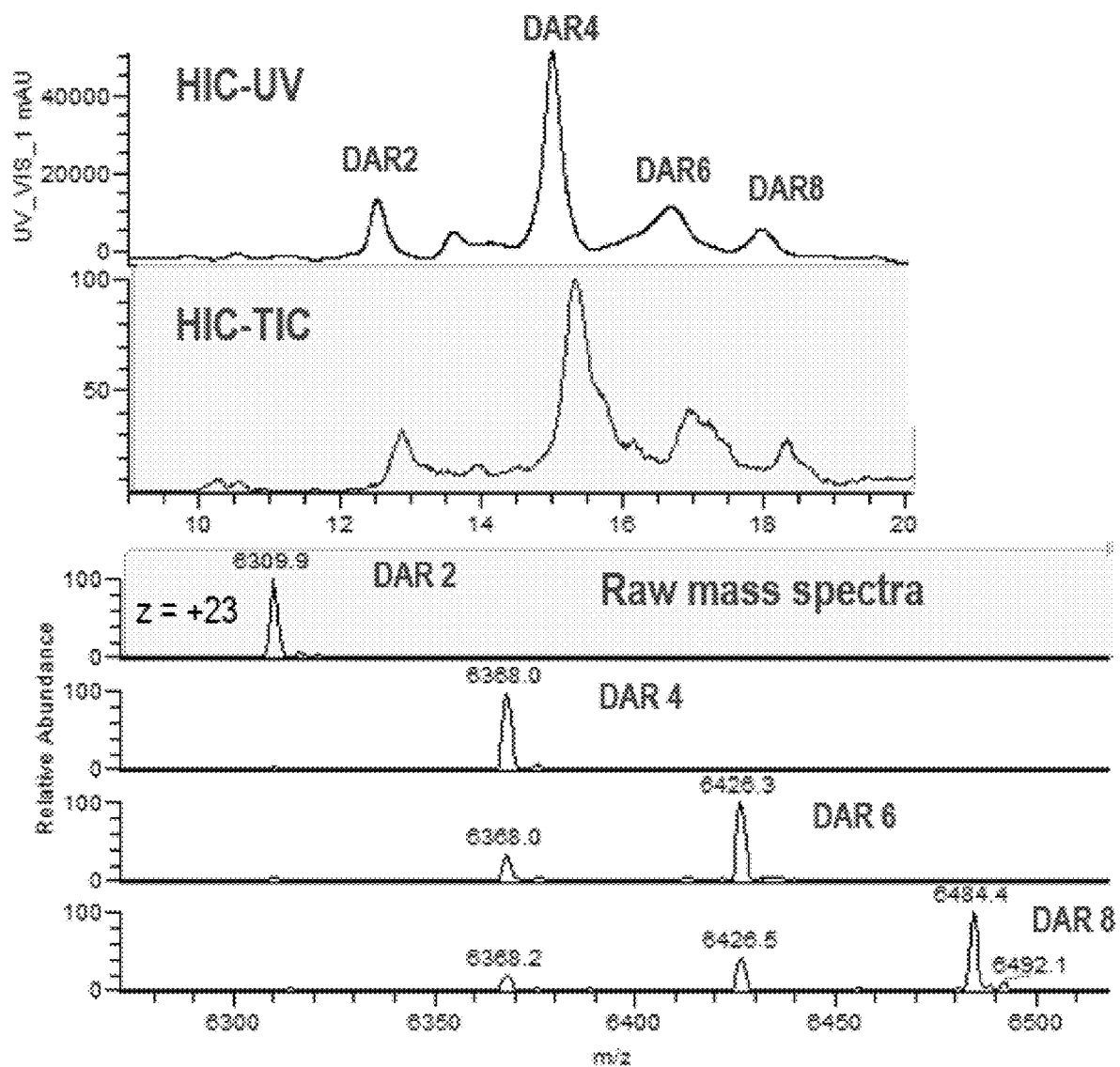
FIG. 12 shows the separation profiles of SigmaMAb Cys-linked ADC mimic using the design B2 of the HIC-native MS of the present application according to an exemplary embodiment.

The HIC separation profile of SigmaMAb Cys-linked ADC mimic was provided by Sigma as shown in FIG. 11. SigmaMAb Cys-linked ADC mimic was tested using the design B2 of the HIC-native MS of the present application. The results of testing design B2 showed good UV resemblance to the HIC profile provided by Sigma. However, the tailing of MS peak was observed with insufficient MS signal intensity as shown in FIG. 12.

Figure 14:
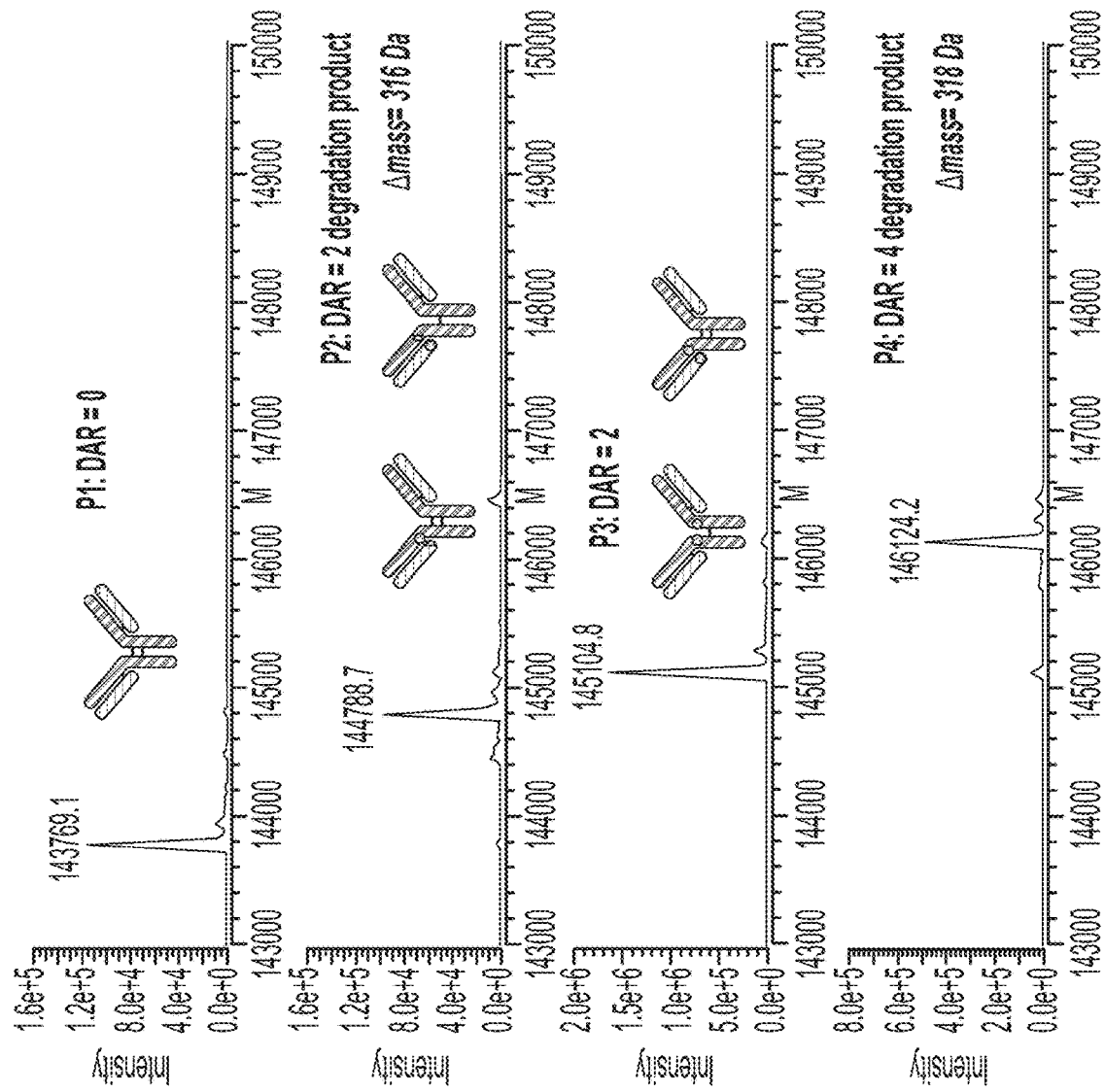
FIG. 14 shows the separation profiles of SigmaMAb Cys-linked ADC mimic corresponding to drug-to-antibody ratio (DAR) of the ADC using the design C of the HIC-native MS of the present application according to an exemplary embodiment.
Figure 14:
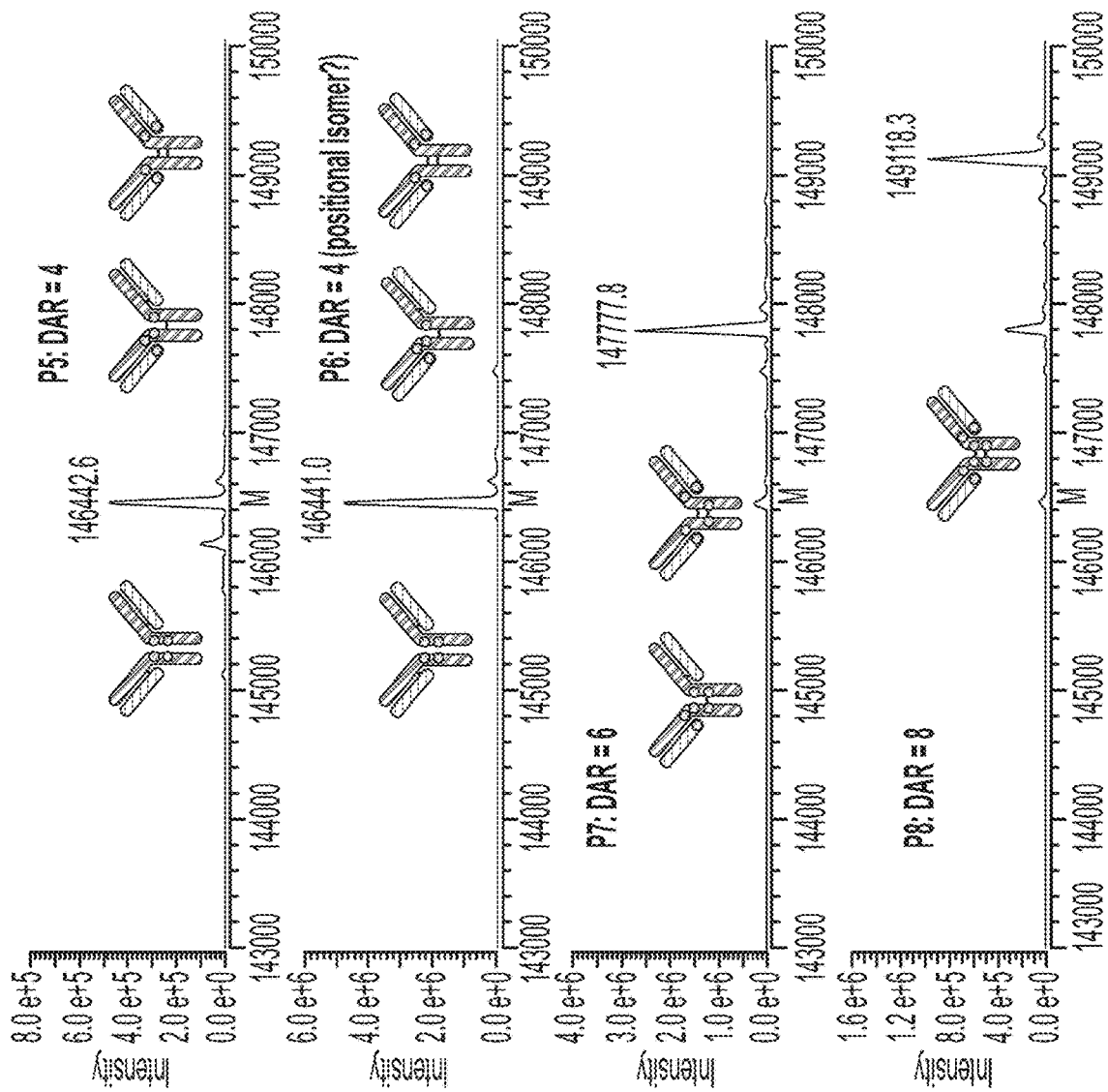
Figure 15:
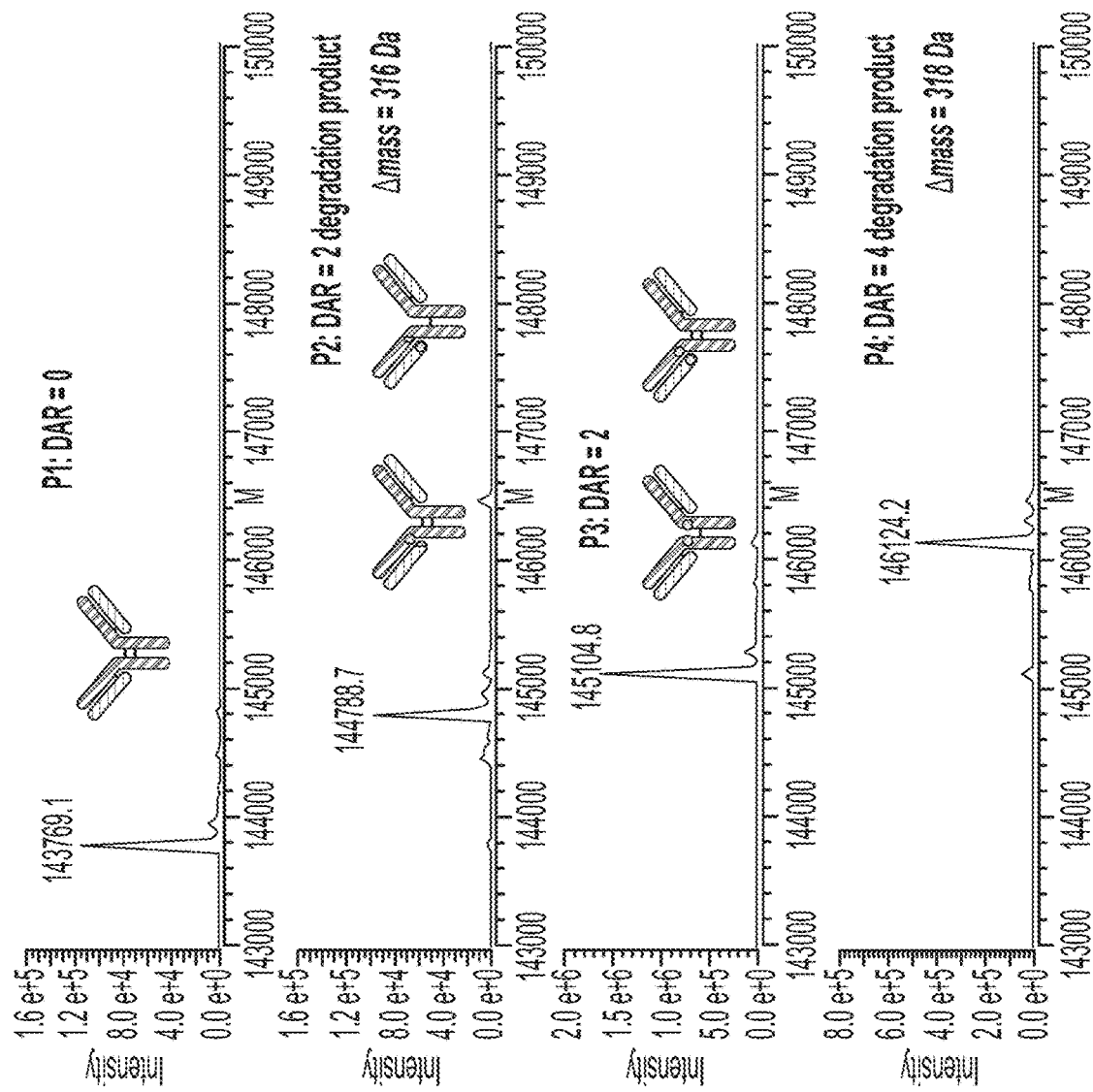
FIG. 15 shows the separation profiles of SigmaMAb Cys-linked ADC mimic including degradation product using the design C of the HIC-native MS of the present application according to an exemplary embodiment.
Figure 15:
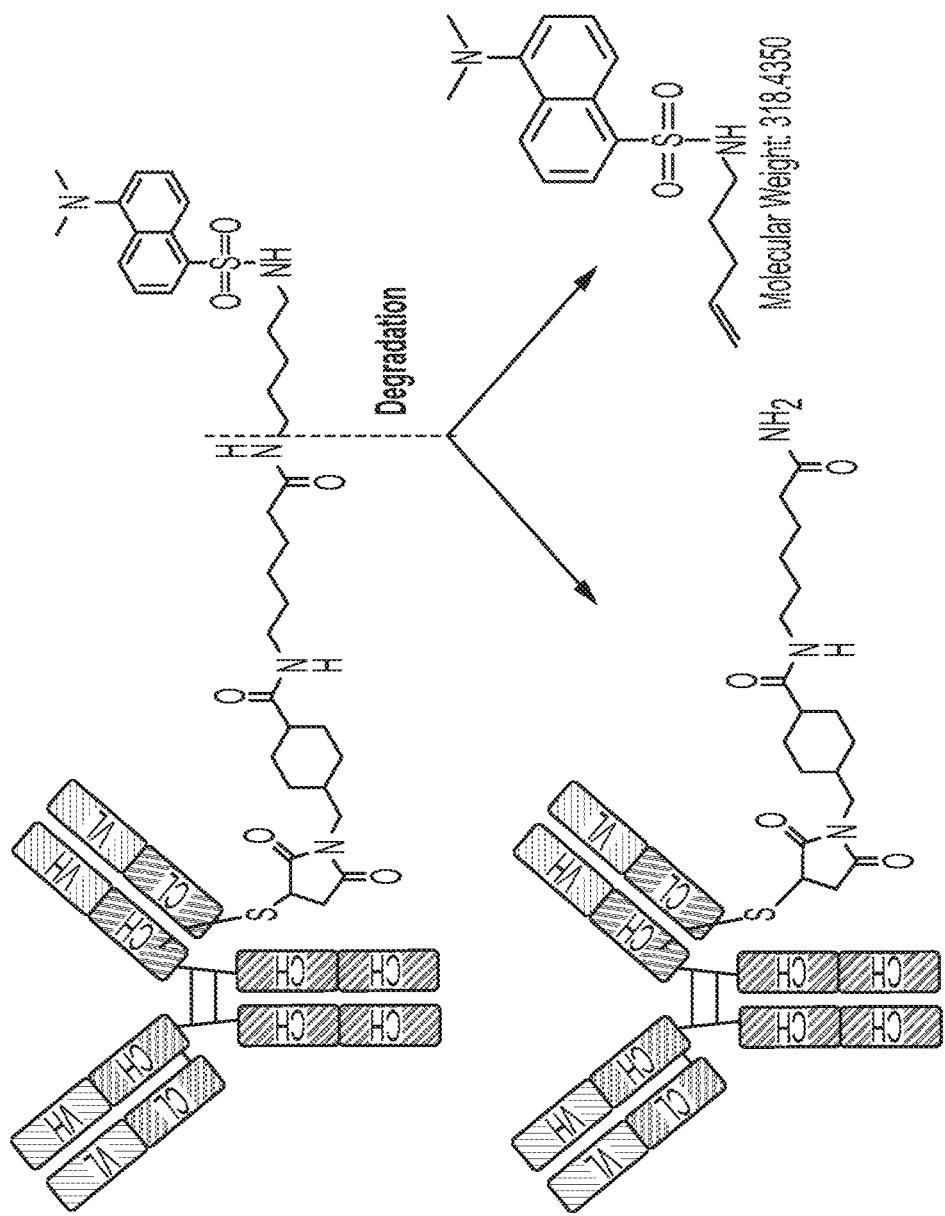

SigmaMAb Cys-linked ADC mimic was tested using the design C of the HIC-native MS of the present application in comparing to the profile provided by Sigma as shown in FIG. 13. The HIC-TIC profile generated by the HIC-native MS of the present application resembles the HIC profile provided by Sigma. Minimum peak tailing was observed with sufficient MS signal intensity. All TIC peaks detected can be assigned based on the mass spectra corresponding to DAR or degradation products as shown in FIG. 14 and FIG. 15.

Example 5. Characterizations of Drug Locations and Positional Isomers in ADC

In order to characterize drug locations and/or positional isomers in ADC, in-source dissociation was performed in combination with the HIC-native MS method of the present application using design C. SigmaMAb Cys-linked ADC mimic was used for the characterizations of drug locations and/or positional isomers. The resultant separation profiles can be identified to characterize the locations of the conjugated drug in heavy chain or light chain in corresponding to the drug-to-antibody ratio including the degradation products and positional isomer as shown in FIG. 16 (DAR=2), FIG. 17 (DAR=2 for degradation products), FIG. 18 (DAR=4) and FIG. 19 (DAR=6 or 8).

Example 6. Characterizations of Modifications in CDR

The methods and systems of the HIC-native MS of the present application was used to characterize the modifications in CDR in monoclonal antibodies, e.g., mAb-7 and mAb-8. As shown in FIG. 20, the HIC-TIC profiles of mAb-7 showed the separation profile of glycosylation variants of mAb-7, for example, main peak, peak 1 (P1) and peak 2 (P2). The raw mass spectrometry spectral data of mAb-7 was deconvoluted using software. The deconvoluted mass spectrum of mAb-7 showed separation profiles of glycosylation variants, which revealed the specific O-glycosylation variants of CDR in mAb-7.

Figure 21:
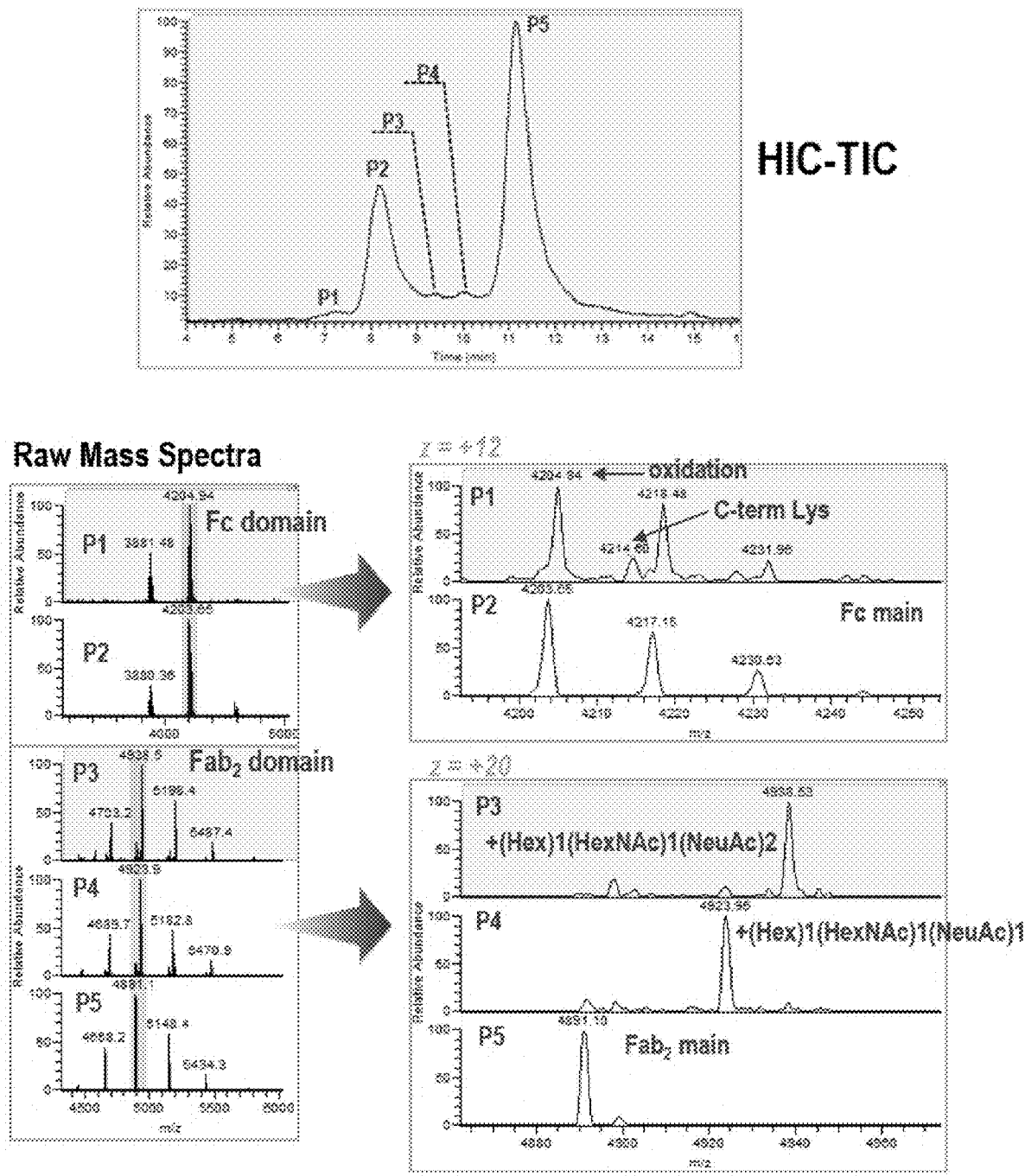
FIG. 21 shows the separation profiles of O-glycosylation variants of digested mAb-7 for characterizing the modifications in CDR including TIC, raw mass spectra and deconvoluted mass spectrum using the HIC-native MS of the present application according to an exemplary embodiment.
Figure 22:
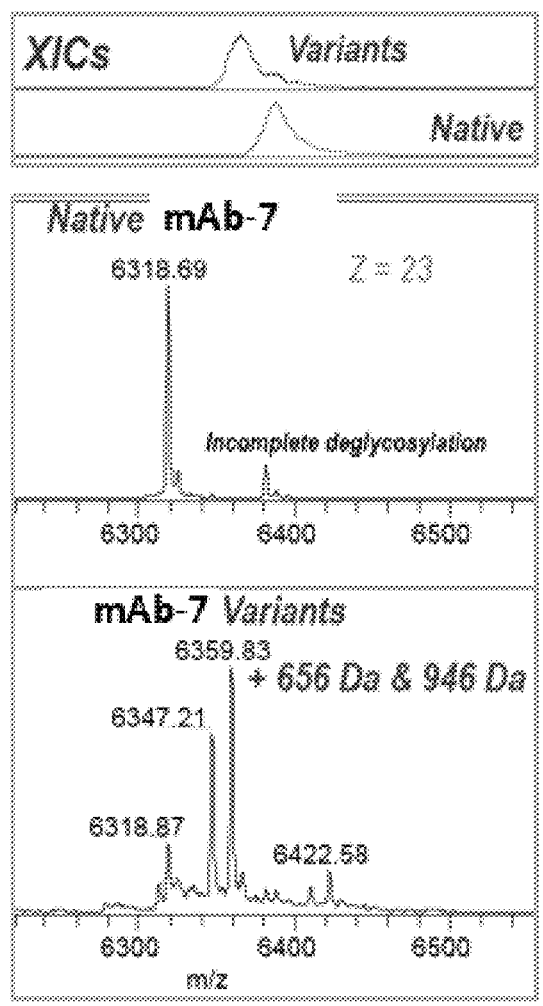
FIG. 22 shows the analysis of O-glycosylation variants of CDR in mAb-7 using native SEC-MS according to an exemplary embodiment.
Figure 23:
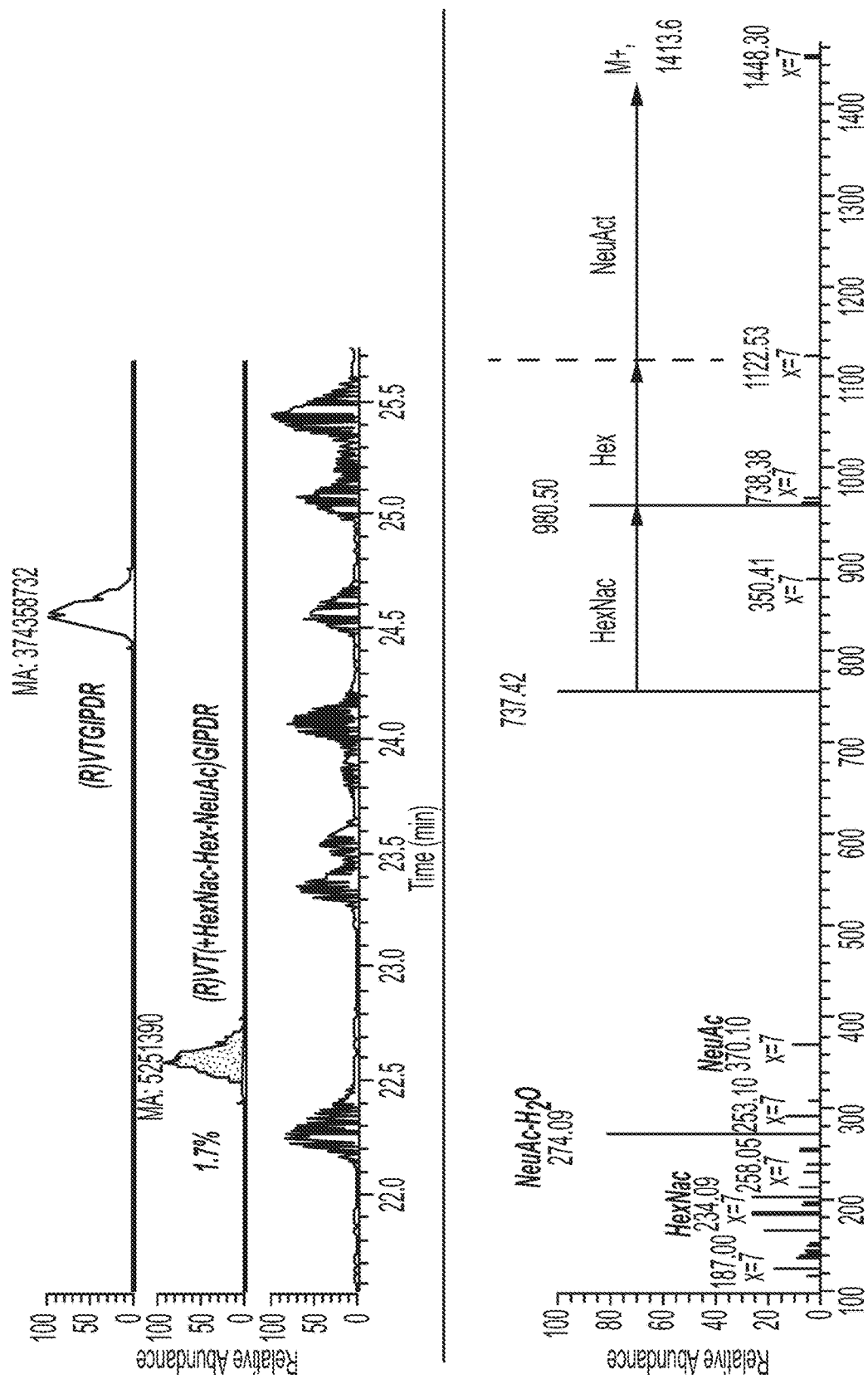
FIG. 23 shows the analysis of O-glycosylation variants of CDR in mAb-7 using reduced peptide mapping according to an exemplary embodiment.

The domain-specific modifications were further characterized by digesting the mAb-7 with FabRICATOR, for example, IdeS which is a cysteine protease that digests antibodies at a specific site below the hinge to generate F(ab')2 and Fc/2 fragments. As shown in FIG. 21, the HIC-TIC profiles of digested mAb-7 showed the separation profile of domain-specific glycosylation variants of mAb-7. The raw mass spectrometry spectral data was deconvoluted using software. The deconvoluted mass spectrum of mAb-7 showed separation profiles of domain-specific glycosylation variants, which revealed the specific O-glycosylation variants of CDR in mAb-7. The O-glycosylation variants of mAb-7 were further analyzed using orthogonal methods including native SEC (size-exclusion chromatography) MS and reduced peptide mapping as shown in FIG. 22 and FIG. 23.

The methods and systems of the HIC-native MS of the present application was used to characterize the modifications in CDR in mAb-8, such as oxidation. As shown in FIG. 24, the HIC-TIC profiles of mAb-8 showed the separation profile of mAb-8 variants, e.g., main peak and peak 1 (P1). The raw mass spectrometry spectral data of mAb-8 was deconvoluted using software. The deconvoluted mass spectrum of mAb-8 showed separation profiles of mass variants, such as mass changes of 15.6 Da, which revealed the specific oxidation in CDR in mAb-8. The oxidation variants of mAb-8 were further analyzed using reduced peptide mapping as shown in FIG. 25. The results revealed the oxidation of methionine at position 54 in heavy chain of mAb-8.

Example 7. Characterizing the Degraded Payload of ADC

Figure 26:
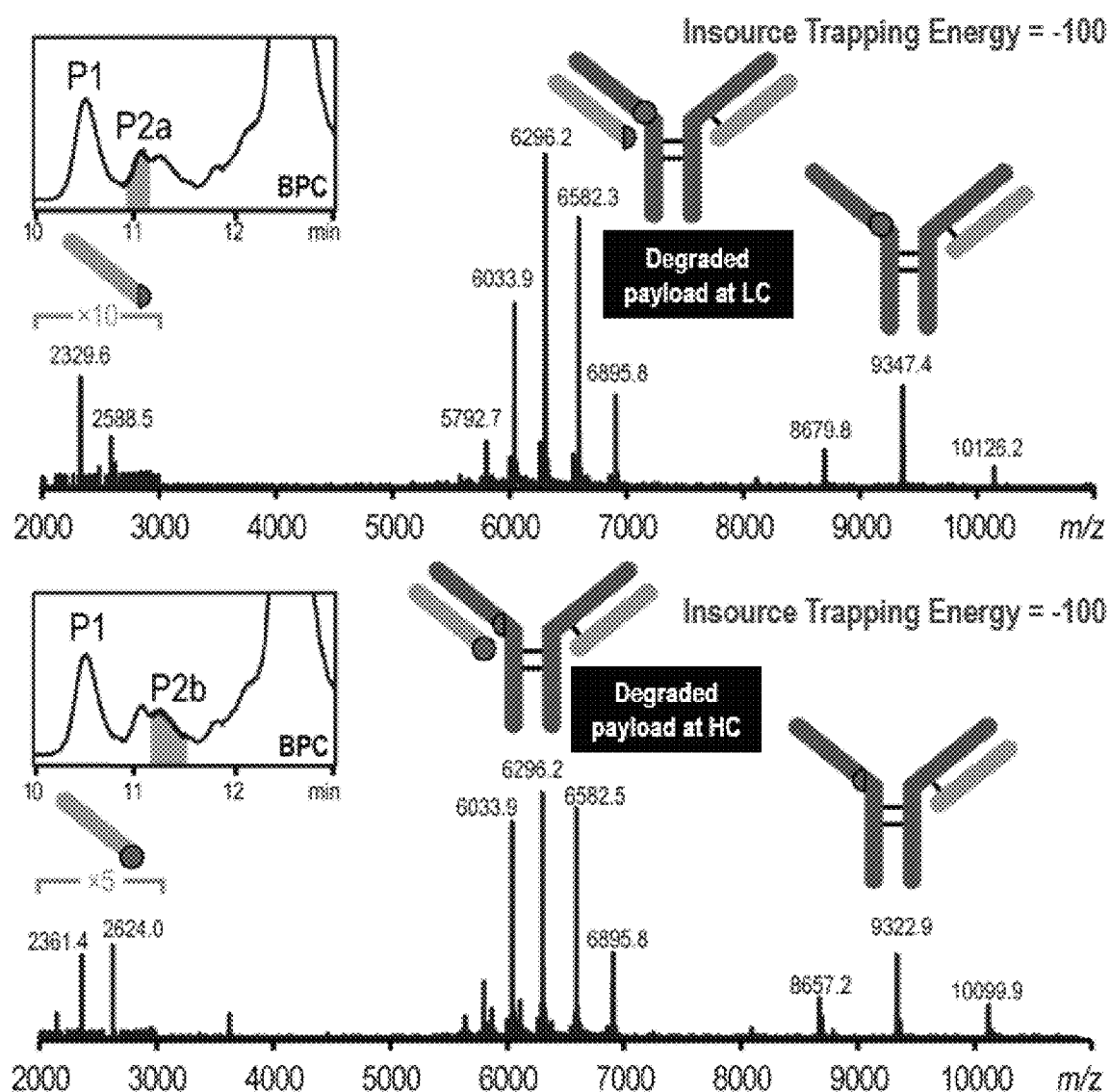
FIG. 26 shows the separation profile of raw mass spectra for characterizing localization of degraded payload in ADC using insource trapping energy in combination with the HIC-native MS method of the present application according to an exemplary embodiment. SigmaMAb Cys-linked ADC mimic was used for the characterizations.
Figure 27:
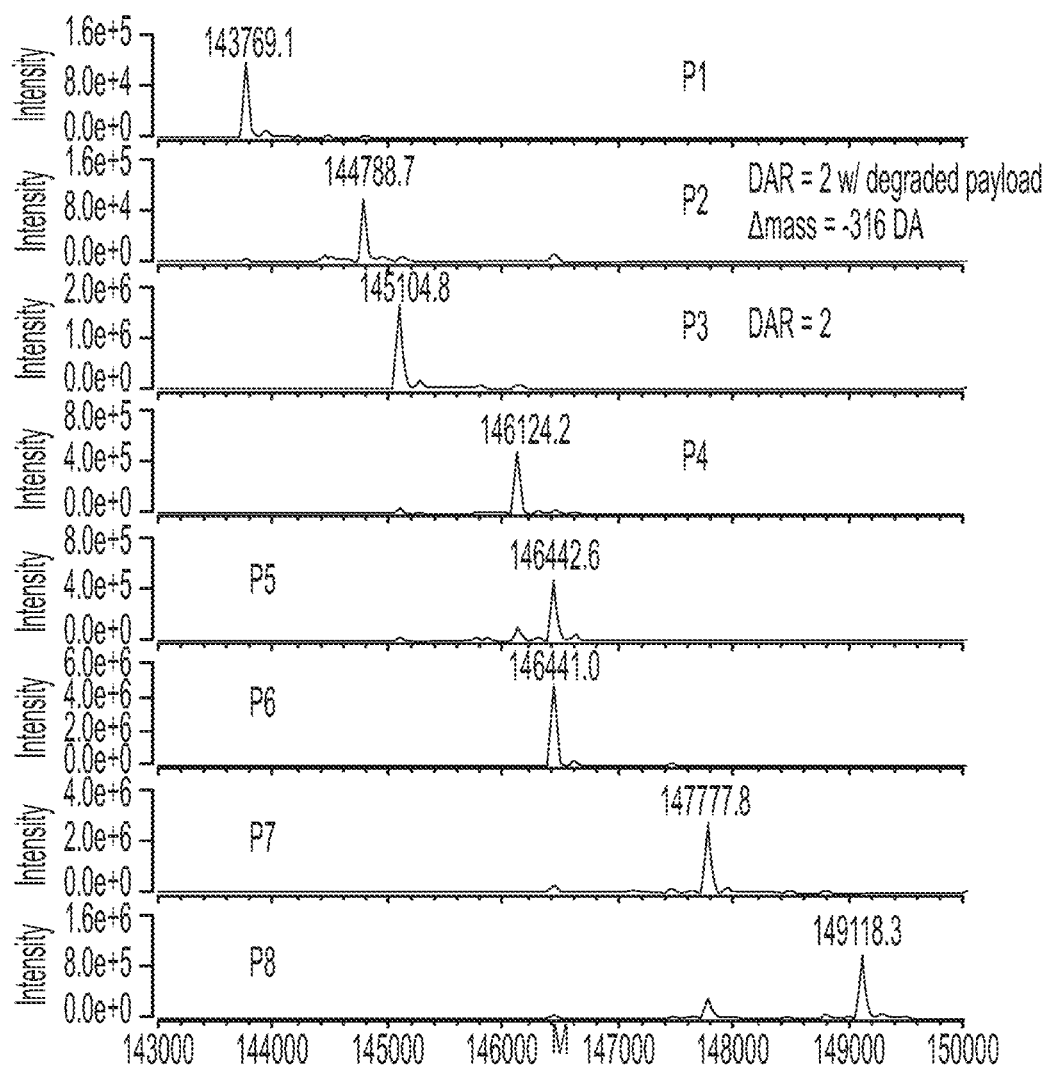
FIG. 27 shows the separation profile of deconvoluted mass spectrum for characterizing localization of degraded payload in ADC using insource trapping energy in combination with the HIC-native MS method of the present application according to an exemplary embodiment. SigmaMAb Cys-linked ADC mimic was used for the characterizations.

In order to characterize localization of degraded payload in ADC, insource trapping energy was performed in combination with the HIC-native MS method of the present application. SigmaMAb Cys-linked ADC mimic was used for the characterizations. The resultant separation profiles can be identified to characterize the degraded payload as shown in FIG. 26 and FIG. 27.

Example 8. Characterizing Molecular Variants of Antibodies

Figure 28:
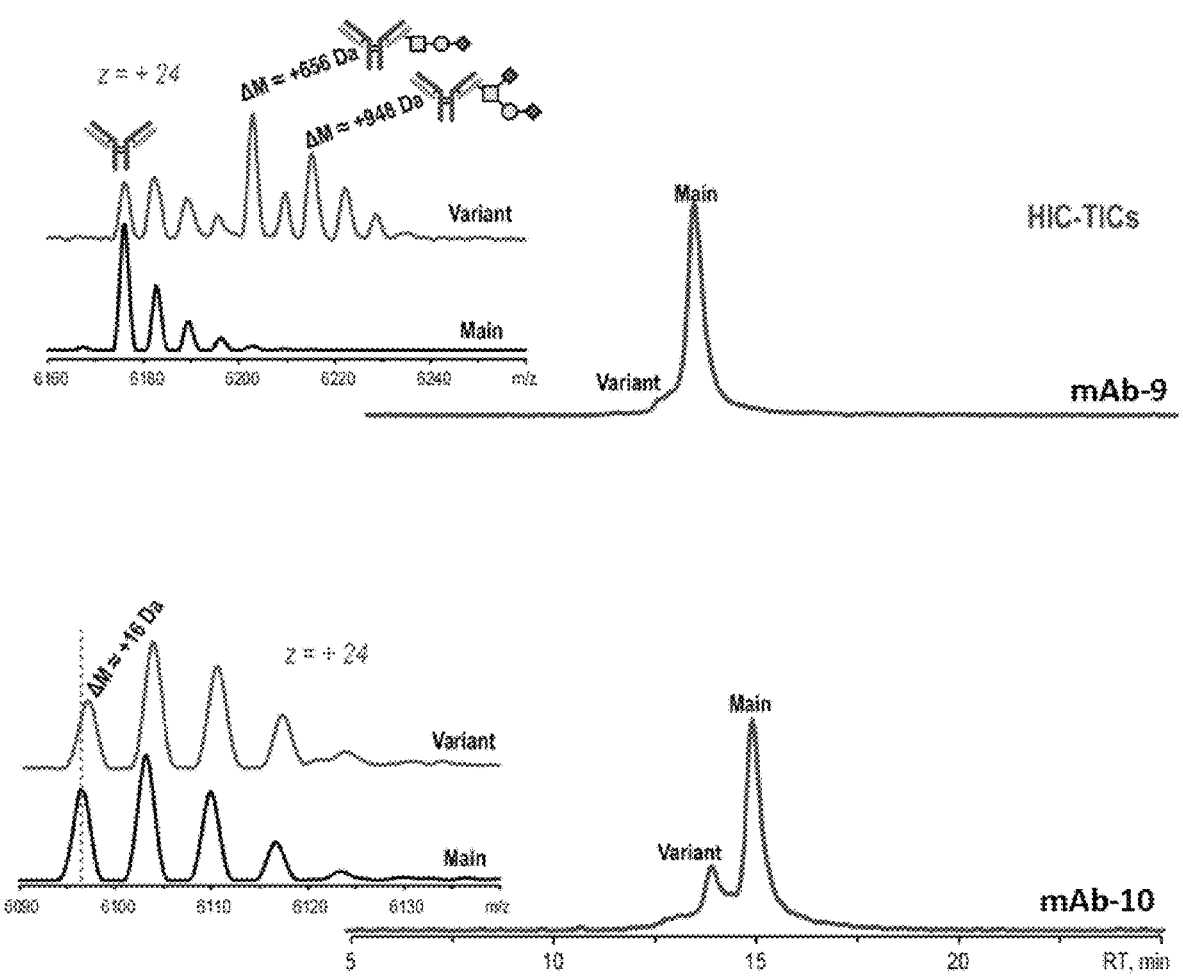
FIG. 28 shows HIC-TIC profiles and mass spectrum for characterizing the molecular variants of monoclonal antibodies, e.g., mAb-9 and mAb-10, using the HIC-native MS of the present application according to an exemplary embodiment.

The methods and systems of the HIC-native MS of the present application was used to characterize the molecular variants of monoclonal antibodies, for example, mAb-9 and mAb-10. As shown in FIG. 28, the HIC-TIC profiles of mAb-9 and mAb-10 showed the separation profile of molecular variants. The mass spectrum showed separation profiles of molecular variants, which revealed the specific mass changes in the molecular variants.

What is claimed is:

1. A method for determining oxidation profiles for at least one peptide or protein in a sample, comprising:
   contacting the sample to a solid surface, wherein the solid surface comprises a hydrophobic group and the solid surface is included in a chromatography column;
   washing the solid surface using a mobile phase to produce at least one eluent, wherein the eluent comprises the at least one peptide or protein;
   determining the oxidation profile of the at least one peptide or protein using a mass spectrometer; and
   determining the oxidation variants in the sample;
   wherein the mass spectrometer is coupled online to the chromatography column.

2. The method of claim 1, further comprising generating at least one separation profile.

3. The method of claim 1, wherein the oxidation variants are oxidized at tryptophan or methionine residues.

4. The method of claim 2, further comprising identifying or quantifying the oxidation variants based on the at least one separation profile.

5. The method of claim 1, wherein the at least one peptide or protein is a drug, an antibody, a bispecific antibody, a monoclonal antibody, a fusion protein, an antibody-drug conjugate, an antibody fragment, or a protein pharmaceutical product.

6. The method of claim 1, wherein the hydrophobic group is phenyl, octyl, butyl, hexyl or propyl.

7. A method for characterizing variants of a peptide or protein in a sample, comprising:
   contacting the sample to a solid surface, wherein the solid surface comprises a hydrophobic group and the solid surface is included in a chromatography column;
   washing the solid surface using a mobile phase to produce at least two eluents, wherein the at least two eluents comprise the peptide or protein and at least one variant thereof;
   obtaining mass measurements of the peptide or protein and at least one variant in the at least two eluents using a mass spectrometer; and
   comparing the mass measurements to identify mass changes in the molecular variants;
   wherein the mass spectrometer is coupled online to the chromatography column.

8. The method of claim 7, wherein the mass spectrometer is run under native conditions.

9. The method of claim 7, further comprising generating at least one separation profile.

10. The method of claim 8, further comprising identifying or quantifying the at least one peptide or protein based on the at least one separation profile.

11. The method of claim 7, wherein the at least one peptide or protein is a drug, an antibody, a bispecific antibody, a monoclonal antibody, a fusion protein, an antibody-drug conjugate, an antibody fragment, or a protein pharmaceutical product.

12. The method of claim 8, further comprising identifying or quantifying changes of masses or relative hydrophobicity of the at least one peptide or protein based on the at least one separation profile or a comparison with another separation profile.

13. The method of claim 8, further comprising identifying or quantifying a drug location, a positional isomer or a degraded payload of the antibody-drug conjugate based on the at least one separation profile or a comparison with another separation profile.

14. The method of claim 8, further comprising identifying or quantifying a modification of a complementarity determining region of the antibody, the bispecific antibody, the monoclonal antibody, the antibody-drug conjugate or the antibody fragment based on the at least one separation profile or a comparison with another separation profile.

15. The method of claim 7, wherein the hydrophobic group is phenyl, octyl, butyl, hexyl or propyl.

* * * * *